US012667711B2

(12) United States Patent
Verkaik et al.

(10) Patent No.: US 12,667,711 B2
(45) Date of Patent: Jun. 30, 2026

(54) VENTRICULAR ASSIST DEVICE AND METHOD

(71) Applicant: MI-VAD, INC., Rochester, MN (US)

(72) Inventors: Josiah Verkaik, Los Gatos, CA (US); James Francis Antaki, Rochester, MN (US); Sudhir Kushwaha, Rochester, MN (US)

(73) Assignee: MI-VAD, INC., Rochester, MN (US)

( * ) Notice: Subject to any disclaimer, the term of this patent is extended or adjusted under 35 U.S.C. 154(b) by 510 days.

(21) Appl. No.: 18/037,214

(22) PCT Filed: Nov. 12, 2021

(86) PCT No.: PCT/US2021/059063
§ 371 (c)(1),
(2) Date: May 16, 2023

(87) PCT Pub. No.: WO2022/108836
PCT Pub. Date: May 27, 2022

(65) Prior Publication Data
US 2023/0405300 A1      Dec. 21, 2023

Related U.S. Application Data

(60) Provisional application No. 63/198,853, filed on Nov. 17, 2020.

(51) Int. Cl.
*A61M 1/12* (2006.01)
*A61M 1/10* (2006.01)
(Continued)

(52) U.S. Cl.
CPC .......... *A61M 60/17* (2021.01); *A61M 60/237* (2021.01); *A61M 60/422* (2021.01);
(Continued)

(58) Field of Classification Search
CPC .............. A61M 60/861; A61M 60/237; A61M 60/422; A61M 60/81; A61M 60/135;
(Continued)

(56) References Cited

U.S. PATENT DOCUMENTS 5,211,546 A      5/1993   Isaacson et al.
8,519,586 B2     8/2013   Terakubo et al.
(Continued)

FOREIGN PATENT DOCUMENTS

CN      103974674 A      8/2014
CN      105338925 A      2/2016
(Continued)

OTHER PUBLICATIONS

PCT/US2021/05906; PCT International Search Report and Written Opinion mailed Apr. 8, 2022.
(Continued)

*Primary Examiner* — Jon Eric C Morales
(74) *Attorney, Agent, or Firm* — MARSHALL, GERSTEIN & BORUN LLP

(57)           ABSTRACT

A ventricular assist device including a frame having a proximal end and an outer surface, and an anchor having a base and a brace coupled to the base. The base is attached to the proximal end of the frame. The device also includes a stator assembly coupled to the frame, a rotor assembly disposed between the stator assembly and the frame, and a power source operatively coupled to the stator assembly. The anchor is moveable between a collapsed configuration in which an inner surface of the brace contacts the outer surface of the frame, and an expanded configuration, in which the inner surface of the brace is offset from the outer surface of the frame and an outer surface of the brace engages a portion of the blood vessel to secure the frame within the blood vessel.

20 Claims, 12 Drawing Sheets

(51) Int. Cl.

| | |
|---|---|
| *A61M 60/17* | (2021.01) |
| *A61M 60/237* | (2021.01) |
| *A61M 60/422* | (2021.01) |
| *A61M 60/562* | (2021.01) |
| *A61M 60/818* | (2021.01) |
| *A61M 60/871* | (2021.01) |

(52) U.S. Cl.
CPC ........ *A61M 60/562* (2021.01); *A61M 60/818* (2021.01); *A61M 60/871* (2021.01)

(58) Field of Classification Search
CPC ................ A61M 60/139; A61M 60/17; A61M 2205/0266; A61M 60/148; A61M 60/174; A61M 60/419; A61M 60/562; A61M 60/569; A61M 60/804; A61M 60/818; A61M 60/825; A61M 60/827; A61M 60/865; A61M 60/871; A61M 60/88; A61M 2205/3331; A61M 2205/3334; A61M 2205/3368; A61M 2205/36; A61M 2210/125; A61M 60/13; A61M 60/178; A61M 60/183; A61M 60/211; A61M 60/216; A61M 60/232; A61M 60/247; A61M 60/30; A61M 60/414; A61M 60/416; A61M 60/515; A61M 60/523; A61M 60/806; A61M 60/812; A61M 60/816; A61M 60/835; A61M 60/873; A61M 60/878; A61M 60/896; A61B 5/026; A61B 5/6847; A61B 5/6869; A61B 5/6876; A61B 8/06; A61B 8/065; A61B 8/0883; A61B 8/12; A61B 8/4416; A61B 8/488; A61F 2/2412; A61F 2/2418; A61F 2/2421; A61N 1/3962

See application file for complete search history.

(56) References Cited

U.S. PATENT DOCUMENTS

| | | | |
|---|---|---|---|
| 2015/0306291 A1 * | 10/2015 | Bonde ................ | A61M 60/865 |
| | | | 600/16 |
| 2017/0216507 A1 | 8/2017 | Kushwaha et al. | |
| 2018/0193543 A1 | 7/2018 | Sun | |
| 2019/0321528 A1 | 10/2019 | Coffman | |

FOREIGN PATENT DOCUMENTS

| | | | |
|---|---|---|---|
| CN | 111107795 | A | 5/2020 |
| DE | 102018208931 | A1 | 12/2019 |
| EP | 3299062 | A1 | 3/2018 |
| JP | 5408423 | B2 | 2/2014 |
| JP | 2017-159083 | A | 9/2017 |
| JP | 2019-526354 | A | 9/2019 |
| WO | WO-2013059747 | A1 | 4/2013 |
| WO | WO-2013/082053 | A1 | 6/2013 |
| WO | WO-2014186107 | A1 | 11/2014 |
| WO | WO-2018/045299 | A1 | 3/2018 |
| WO | WO-2019/135767 | A1 | 7/2019 |
| WO | WO-2019157116 | A1 | 8/2019 |

OTHER PUBLICATIONS

Office Action, European patent application No. 21824137.0-1009, mailing date Jul. 23, 2025.

Japanese Patent Application No. 2023-553158, Notice of Reasons for Refusal, mailing date of Oct. 14, 2025.

Chinese Patent Application No. 202180080809.8, Office Action, dated Jan. 20, 2026.

Indian Patent Application No. 202347040220, Examination Report, dated May 12, 2026.

\* cited by examiner

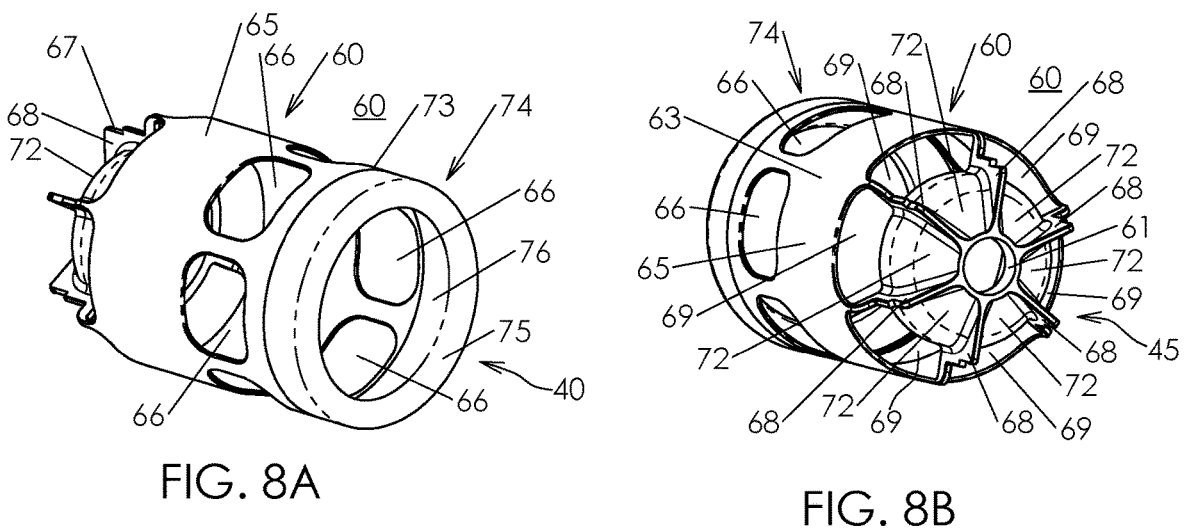
FIG. 8A
FIG. 8B
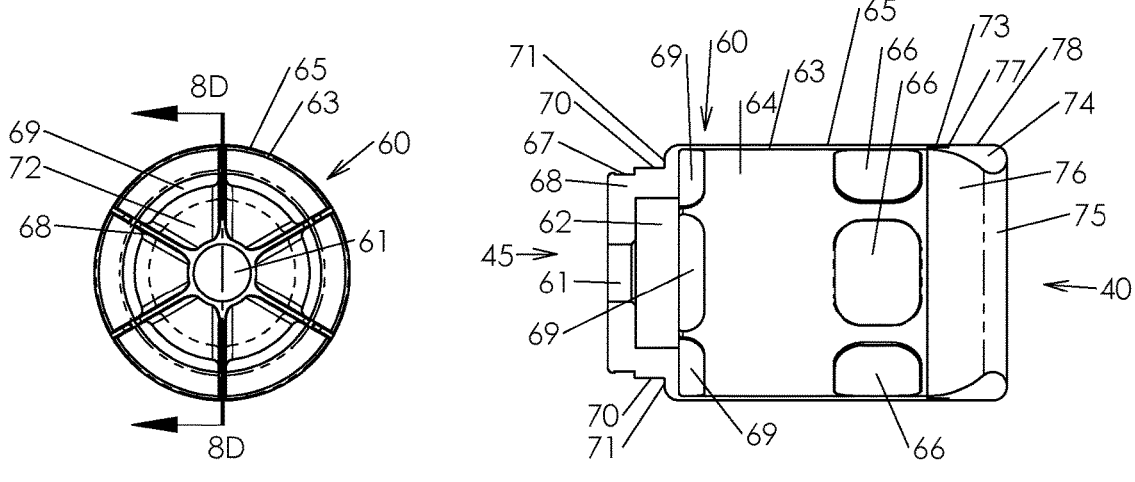
FIG. 8C
FIG. 8D

VENTRICULAR ASSIST DEVICE AND METHOD

CROSS-REFERENCE TO RELATED APPLICATIONS

This patent application is a national stage application of PCT/US21/59063 filed Nov. 12, 2021, which claims priority to U.S. Provisional Patent Application No. 63/198,853 filed on Nov. 17, 2020. The entire contents of these applications are incorporated herein by reference in their entirety.

FIELD OF THE INVENTION

The present invention relates to a ventricular assist device and, more specifically, to a ventricular assist device that is supported with a vessel to augment the pulmonary or systemic circulation.

BACKGROUND

Left ventricular assist devices are now a therapeutic option in patients with end-stage dilated cardiomyopathy. Existing devices are designed for use in severe left ventricular failure. These existing devices have little adaptability for support of the right sided circulation, in particular, are not well-suited for right ventricular failure. Current device designs also tend to be appropriate for patients with dilated cardiomyopathy, but these devices are not well-suited for use in patients with restrictive cardiomyopathy. Unfortunately, the outcome has been poor for past attempts to use existing devices with restrictive cardiomyopathy.

Additionally, further problems with the present generation of devices include the risk of thrombus formation and the risk of infection, as well as negative effects of non-physiologic (non-pulsatile) flow. Non-physiologic flow can potentially cause a number of side-effects, including a high prevalence of gastrointestinal and/or cerebral bleeding. The etiology of the gastrointestinal bleeding is in part related to the non-physiologic flow and may also be related to the depletion of clotting factors within the blood which may be destroyed by such a non-physiologic assist device. Some existing devices are known to have a 30% incidence of clotting factor depletion.

Current devices also may be difficult to use in the setting of an acute myocardial infarction. In such a situation, the freshly infarcted myocardial tissue may be friable, particularly if the location is apical or anterior. Consequently, use of existing devices may not be feasible because of the apical placement of the inflow cannula.

SUMMARY

In accordance with one aspect, a ventricular assist device for a human heart comprises a frame having a proximal end and an outer surface, and the frame is sized for placement within a blood vessel at a selected location within the blood vessel. The device also includes an anchor having a base and a brace coupled to the base. The base is attached to the proximal end of the frame, and the brace has an inner surface and an outer surface. A stator assembly is disposed within and coupled to the frame, a rotor assembly is disposed between the stator assembly and the frame, and a power source is operatively coupled to the stator assembly. The stator assembly and the rotor assembly are arranged to interact in response to the application of power from the power source to the stator assembly to cause the rotor assembly to rotate. So configured, the anchor is moveable between a collapsed configuration in which the inner surface of the brace contacts the outer surface of the frame, and an expanded configuration, in which the inner surface of the brace is offset from the outer surface of the frame and the outer surface of the annular brace engages a portion of the blood vessel to secure the frame within the blood vessel.

In accordance with another example, a ventricular assist device for a human heart comprises a frame having a proximal end, a distal end, a shroud disposed between the proximal end and the distal end and having an inner surface defining a portion of a flow path, and a plurality of projections disposed at the proximal end. The frame is sized for placement within a blood vessel at a selected location within the blood vessel. The device also includes an anchor having a base and a brace coupled to the base, the anchor moveable to an expanded configuration in which the brace is offset from frame and engages a portion of a blood vessel. In addition, a stator assembly is disposed within the frame, a rotor assembly is disposed between the stator assembly and the frame, and a power source is operatively coupled to the stator assembly. The stator and the rotor are arranged to interact in response to the application of power from the power source to the stator assembly to cause the rotor assembly to rotate. So configured the plurality of projections of the frame engage the base of the anchor.

In accordance with yet another aspect, a method of implanting a ventricular assist device in a heart comprises the steps of selecting a frame sized for placement within a blood vessel at a selected location within the blood vessel, and the frame has an inner surface defining a flow path, a stator assembly disposed within the frame, and a rotor assembly disposed between the frame and the stator assembly. The method further includes attaching an annular base of an anchor to a proximal end of the frame, and placing the anchor at the selected location in a collapsed configuration. The method still further includes expanding the anchor at the selected location to secure the frame to the selected location, operatively coupling a power source to the stator assembly; and controlling the power source to cause the rotor assembly to rotate.

In accordance with yet another aspect of the present disclosure, a ventricular assist device for a human heart comprises a frame having a proximal end and an inner surface defining a flow path and an anchor coupled to the proximal end of the frame and moveable between a collapsed configuration and an expanded configuration. The expanded configuration is a configuration in which a portion of the anchor is offset from the frame and engages a portion of a blood vessel. The device further includes a stator assembly disposed within the frame, a rotor assembly disposed between the stator assembly and the frame, and a power source operatively coupled to the stator assembly. The stator assembly and the rotor assembly are arranged to interact in response to the application of power from the power source to the stator to cause the rotor assembly to rotate. The device also includes a feedthrough assembly disposed within the stator assembly. The feedthrough assembly has an outer surface for interfacing with the stator assembly, a feedthrough cover with a proximal end and a distal end, a feedthrough flange disposed at the distal end of the feedthrough cover, and a plurality of insulators seated within the feedthrough flange. So configured, the feedthrough cover and the feedthrough flange are used to form an enclosure for the stator assembly.

According to yet another aspect, a ventricular assist device for a human heart comprises a frame having a proximal end and an anchor coupled to the proximal end of the frame and moveable between a collapsed configuration and an expanded configuration. The expanded configuration is a configuration in which a portion of the anchor is offset from the frame and engages a portion of a blood vessel. The device also includes a stator assembly disposed within the frame, and the stator assembly comprises a stator housing having a sleeve, a thrust bearing surface integral with the sleeve, and an internal area. The device further includes a rotor assembly disposed between the stator assembly and the frame and a power source operatively coupled to the stator assembly. The stator assembly and the rotor assembly are arranged to interact in response to the application of power from the power source to the stator assembly to cause the rotor assembly to rotate. In addition, the stator housing defines a hermetically sealed assembly, sealing off the internal area of the stator housing.

In accordance with still yet another aspect, a ventricular assist device for a human heart comprises a frame having a proximal end, an anchor coupled to the proximal end of the frame and adapted to engage a portion of a blood vessel, and a stator assembly disposed within the frame. The device further includes a rotor assembly disposed between the stator assembly and the frame. The rotor assembly comprises a rotor housing having a distal end, a proximal end, a sleeve, a thrust bearing surface integral with the sleeve, and a flange disposed at the proximal end of the sleeve. The rotor assembly also comprises an impeller shell disposed along the length of the sleeve between the distal and proximal ends of the rotor housing, and the impeller shell forms an internal area between the impeller shell and the rotor housing. The device further includes a power source operatively coupled to the stator assembly, and the stator assembly and the rotor assembly are arranged to interact in response to the application of power from the power source to the stator assembly to cause the rotor assembly to rotate. The impeller shell and the rotor housing together define a hermetically sealed rotor assembly, sealing off the internal area between the impeller shell and the rotor housing.

In accordance with yet another aspect of the present disclosure, a ventricular assist device for a human heart comprises a frame having a proximal end, a distal end, a plurality of fenestrations, and an external surface. The device further includes an anchor that is coupled to the proximal end of the frame and adapted to engage a portion of a blood vessel, a stator assembly disposed within the frame, and a rotor assembly disposed between the stator assembly and the frame, the rotor assembly including an impeller shell. A power source is operatively coupled to the stator assembly, and the stator assembly and the rotor assembly arranged to interact in response to the application of power from the power source to the stator assembly to cause the rotor assembly to rotate. The device still further includes a primary flow path defined by an annular inlet disposed at the distal end of the frame, the plurality of fenestrations in the frame, an impeller zone disposed between an external surface of the frame and the impeller shell of the rotor assembly, and an annular outlet disposed at the proximal end of the frame. So configured, fluid in the primary flow path is drawn through the annular inlet and the plurality of fenestrations into the impeller zone, and exits out of the annular outlet disposed at the proximal end. The device also includes a secondary flow path defined by the annular inlet, the impeller zone, an axial rotor gap disposed between the frame and the rotor assembly, a radial rotor gap disposed between the stator assembly and the rotor assembly, and a plurality of through-holes of the rotor housing. So configured, fluid in the secondary flow path is drawn through the impeller zone and passes through the axial rotor gap, the radial rotor gap, and the plurality of through-holes of the rotor assembly, exiting at the distal end of the frame.

According to another aspect of the present disclosure, a ventricular assist device for a human heart comprises a frame having a proximal end, a distal end, an inside surface, and at least one proximal slot. The device further includes an anchor coupled to the proximal end of the frame and adapted to engage a portion of a blood vessel, a stator assembly disposed within the frame, and a rotor assembly disposed between the stator assembly and the frame, the rotor assembly including an impeller shell and a plurality of through-holes. The device also includes a primary flow path defined by at least one proximal slot disposed at the proximal end of the frame, an impeller zone disposed between the impeller shell and an inside surface of the frame, and an annular outlet disposed at the distal end of the frame. So configured, fluid in the primary flow path is drawn through the at least one proximal slot and into the impeller zone and ejected from the annular outlet disposed near the distal end of the frame. The device still further includes a secondary flow path defined by the plurality of through-holes in the rotor assembly, an annular rotor gap disposed between the stator assembly and the rotor assembly, and an axial gap at the proximal end of the frame. So configured, fluid in the secondary flow path is drawn through the plurality of through-holes, the annular rotor gap, and the axial gap, and is ejected from the annular outlet.

It will be recognized that any of the foregoing aspects may be combined with or modified in light of the other aspects disclosed herein, as desired. In addition, any one of the foregoing devices or methods may include any one or more of the following features.

According to one aspect, the anchor may further comprise at least one strut extending from the base to the brace, the at least one strut coupling the brace to the base. In addition, the brace may further comprise an annular brace comprising a plurality of distal junctions, and a plurality of cross beams, the plurality of cross beams connecting the plurality of distal junctions to the plurality of proximal junctions. The annular brace may further comprise a plurality of prongs centered along the plurality of proximal junctions to further support the anchor within the blood vessel, each prong having a prong tip to distribute pressure and prevent excessive stress concentration to the blood vessel. The brace may further comprise an annular brace having an outer diameter capable of expanding to a maximum outer diameter of approximately 30 mm in the expanded configuration, in which the annular brace deflects inwardly such that the outer diameter is smaller than the maximum outer diameter due at least in part to reaction forces applied to the annular brace by the blood vessel. In another example, the anchor may comprise shape-settable Ni—Ti super elastic alloy, such as nitinol. In another example, the device may further comprise a lead extending from the proximal end of the frame, and the lead is adapted to be coupled to a controller.

According to another aspect, the frame may further comprise a plurality of outer slots disposed at the proximal end and a plurality of diffuser zones disposed adjacent to the plurality of outlet slots, such that exiting fluid flows between the plurality of outlet slots and along the plurality of diffuser zones. The frame may further comprise a plurality of outlet slots disposed at the proximal end and a plurality of diffuser zones disposed adjacent to the plurality of outlet slots, such that exiting fluid flows between the plurality of outlet slots and along the plurality of diffuser zones. In addition, the frame may further comprise a feedthrough bore disposed at the proximal end and a stator bore disposed near the proximal end, the stator bore having a diameter greater than a diameter of the feedthrough bore, and the stator bore for receiving a portion of the stator assembly. Further, each projection of the plurality of projections including a proximal slot for interfacing with the base of the anchor. Still further, the frame may further include a proximal outer surface and a proximal shoulder extending to the shroud, the shroud may include an elongate wall and a shroud outer surface, the proximal outer surface of the frame may have a diameter less than a diameter of the shroud outer surface and about the same as a diameter of the base of the anchor. In another example, the distal end of the frame may have a plurality of distal fenestrations.

According to another aspect, the device may further comprise a guard disposed at the distal end of the frame, and the frame may further comprise a guard interface, such that the guard couples to the guard interface of the frame. The guard may also include one or more of a distal lip, an expansion zone, a seam, and an outer surface, and the outer surface may have an outer diameter about the same as an outer diameter of the shroud external surface, where the distal lip, the expansion zone, and the shroud inner surface define a primary stationary interior flow surface. In addition, the selected location of one of the distal end or the proximal end of the frame may be one or more of: near an aortic root proximate to the aortic valve and downstream from the coronary artery; or upstream an aorta arch in an ascending aorta before a lesser curve and a greater curve of a human heart. a motor stator assembly disposed within the stator assembly, and the motor stator assembly may be coupled to a controller by a lead extending from the proximal end of the frame.

According to yet another aspect, the stator assembly may include a plurality of stator bearing magnets disposed near the proximal end, and the rotor assembly may further comprise a plurality of rotor bearing magnets disposed near the proximal end, such that the plurality of stator bearing magnets and the plurality of rotor bearing magnets together comprise a radial magnetic bearing positioned near the proximal end of the rotor assembly.

In addition, the plurality of stator bearing magnets may be axially magnetized and stacked in opposing polarity, and the plurality of rotor bearing magnets may be axially magnetized and stacked in opposing polarity. So configured, the stator bearing magnet and the rotor bearing magnet may interact and create a radial magnetic field to support the proximal end of the rotor assembly in a substantially coaxial position relative to the stator assembly.

According to yet another aspect, the stator assembly may include a plurality of stator bearing magnets and the rotor assembly may include a plurality of rotor bearing magnets, such that at least one stator bearing magnet and at least one rotor bearing magnet are in magnetic opposition to each other, providing a radial bearing support. In addition, the stator assembly may include a plurality of stator bearing magnets and the rotor bearing assembly may include a plurality of rotor bearing magnets, wherein an axial position of the plurality of rotor bearing magnets may be offset relative to an axial position of the plurality of stator bearing magnets toward a proximal end, producing an axial force that biases the rotor assembly toward the proximal end and ensures contact between the stator assembly and the rotor assembly is maintained along a thrust bearing surface. Further, the device may comprise a thrust bearing disposed at the distal end of the frame, and the thrust bearing may comprise a convex thrust bearing surface of the stator assembly that fits into a concave thrust bearing surface of the rotor assembly. The convex thrust bearing surface may include a semi-spherical ball shape and the concave thrust bearing surface may include a cup-shape, such that the thrust bearing surface interface is disposed between the convex thrust bearing surface and the concave thrust bearing surface. In addition, a substrate material that defines each of the concave thrust bearing surface of the rotor assembly and the convex thrust bearing surface of the stator assembly may be zirconia ceramic. Further, the distal end of the frame may be adapted to be disposed near an aortic root proximate to an aortic valve and downstream from a coronary artery. wherein a fluid flow rate through the secondary flow path is less than the fluid flow rate through the primary flow path.

According to another aspect, fluid forces may maintain radial support of the rotor assembly while the rotor assembly rotates. Further, the annular rotor gap may be a hydrodynamic bearing.

According to yet another aspect, the secondary flow path may be further defined by one or more of a collector zone disposed at the distal end of the frame, a convergence zone disposed between the stator assembly and the rotor assembly at the distal end of the frame, and a bearing bypass zone adjacent to a thrust bearing surface interface. So configured, fluid in the secondary flow path may be drawn through one or more of the collector zone, the convergence zone, and the bearing bypass zone, and is again being ejected at the annular outlet of the frame at the distal end.

According to yet another aspect, a motor stator assembly of the stator assembly may interact with a plurality of motor magnets for the rotor assembly to rotate the rotor assembly. In addition, an axial length of the anchor is approximately equal to an axial length of the frame, and a portion of the rotor assembly may outwardly extends from the distal end of the frame. Further, the proximal end of the frame may be adapted to be disposed near an aortic root proximate to the aortic valve and downstream from the coronary artery. Still further, the rotor assembly may further include a concave thrust bearing surface, and the stator assembly may further include a convex thrust bearing surface disposed adjacent to the concave thrust bearing surface. Each of the concave thrust bearing surface of the rotor assembly and the convex thrust bearing surface of the stator assembly may include a ceramic substrate. Further, the rotor assembly may further include a plurality of motor magnets offset relative to a motor stator assembly of the stator assembly. The motor stator assembly may include a magnetically susceptible material that interacts with the plurality of motor magnets of the rotor assembly, causing a magnetic force in an axial direction to maintain contact between the stator assembly and the rotor assembly when the device is not operating.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings. For descriptive purposes, the "distal" end refers to the end opposite from projection of the electrical lead and the "proximal" end refers to the end in which electrical lead extends from the device corresponding to the exemplary embodiment shown in the figures, unless otherwise noted herein.

FIG. 1 is a sectional posterior view of a human heart with a ventricular assist device of the present disclosure shown in an approximate relative position within an ascending aorta according to an exemplary embodiment of the invention.

Figure 1:
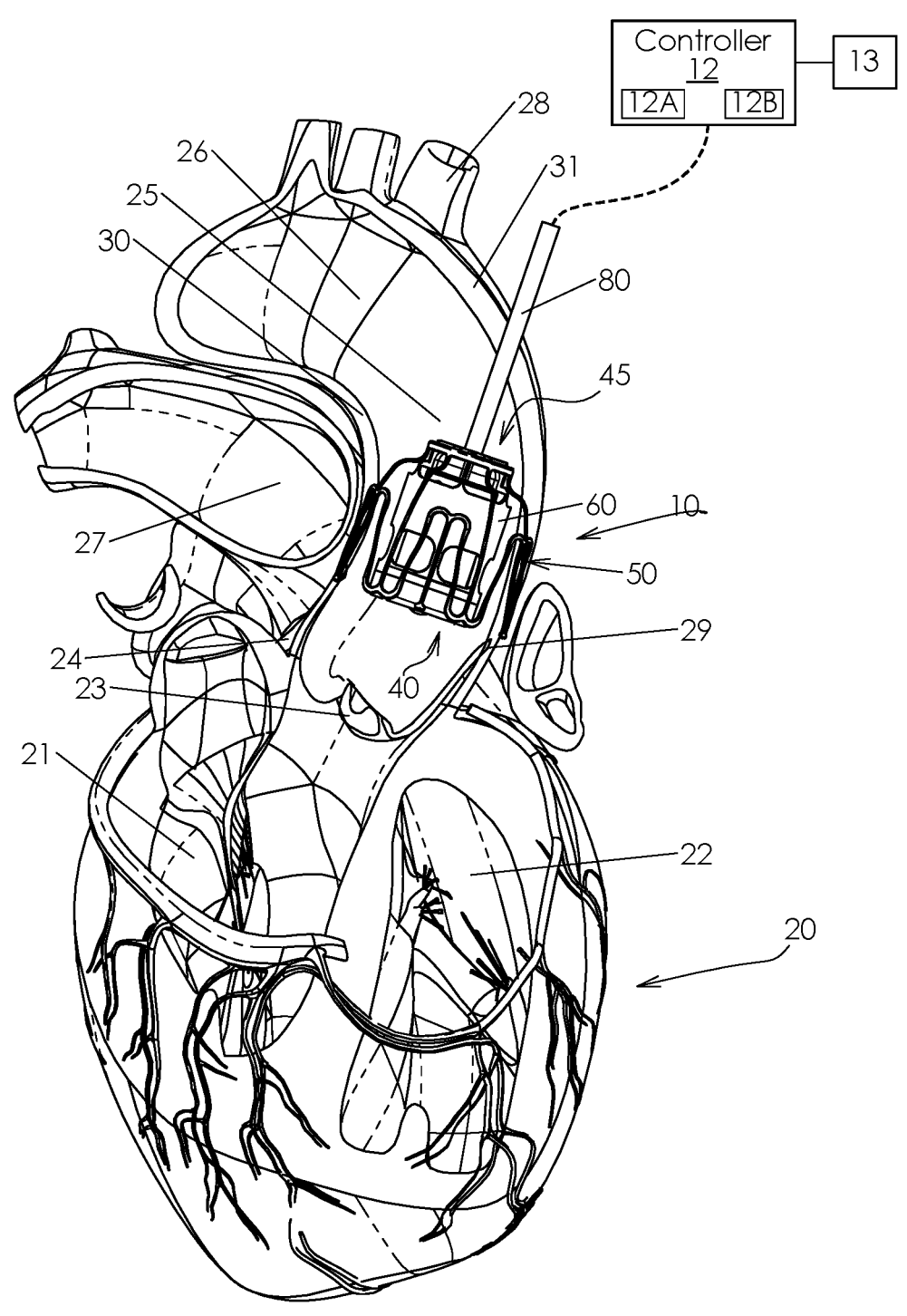
Figures 2A, 2B, 3A, 3B:
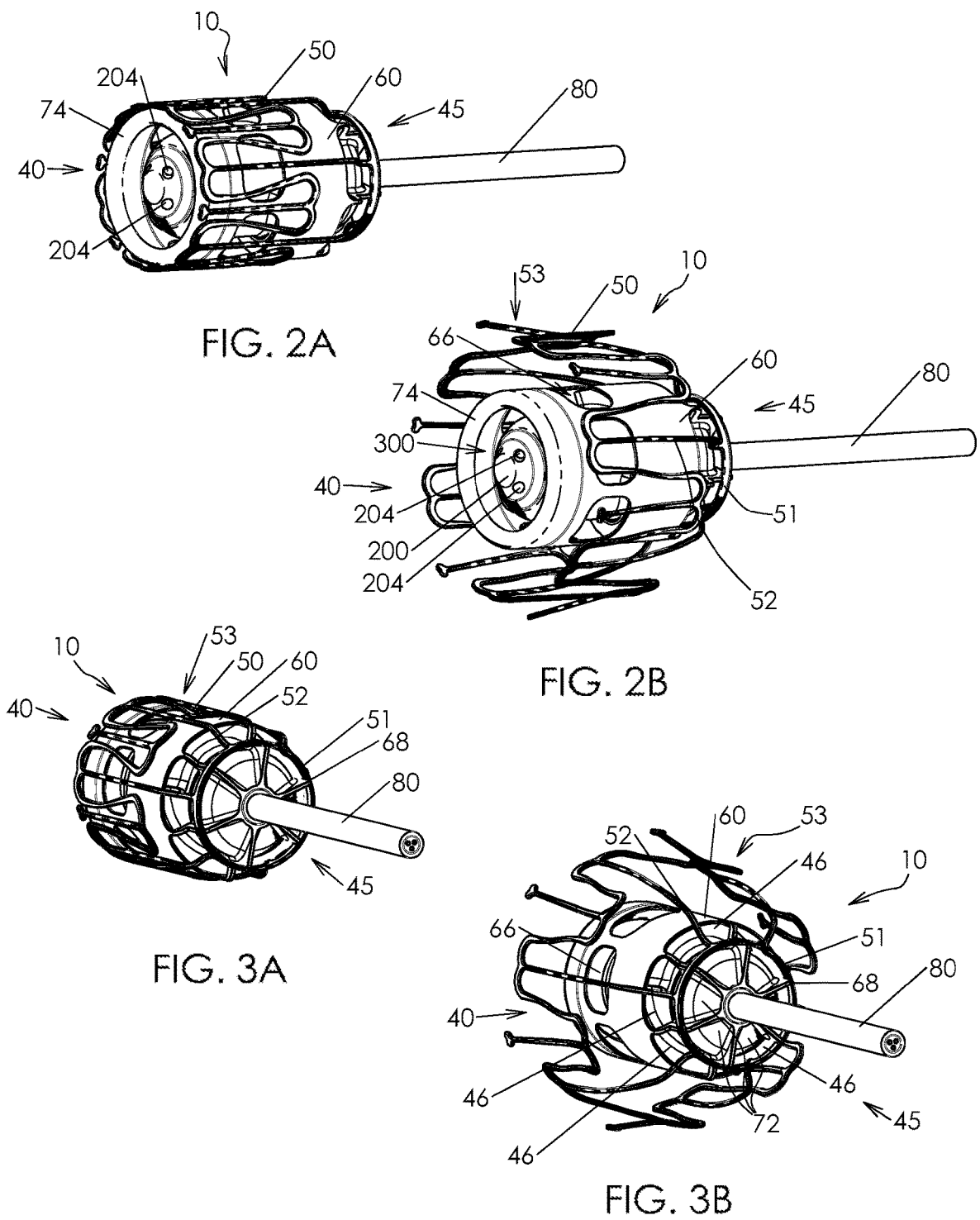

FIG. 2A-2B are perspective views of a distal end of the device of FIG. 1 according to the exemplary embodiment. FIG. 2A depicts an anchor of the device in a collapsed configuration, and FIG. 2B shows the anchor in an expanded configuration.

FIG. 3A-3B are perspective views of a proximal end of the device according to the exemplary embodiment. FIG. 3A depicts the anchor in the collapsed configuration, and FIG. 3B depicts the anchor in the expanded configuration.

Figure 4A:
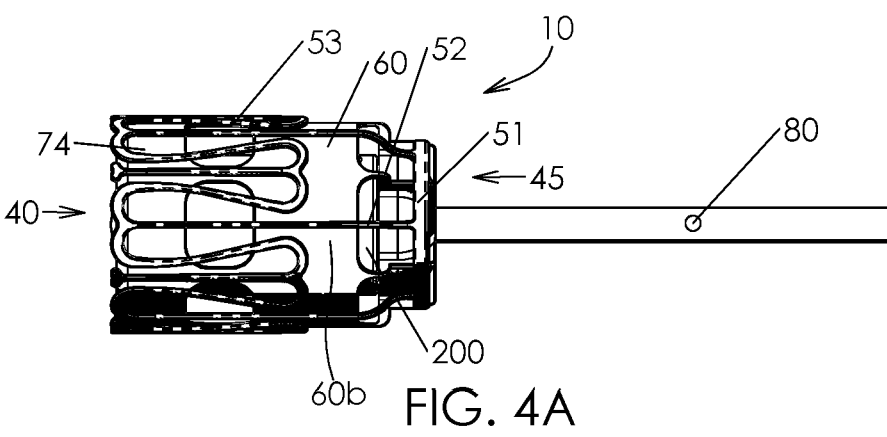
Figure 4B:
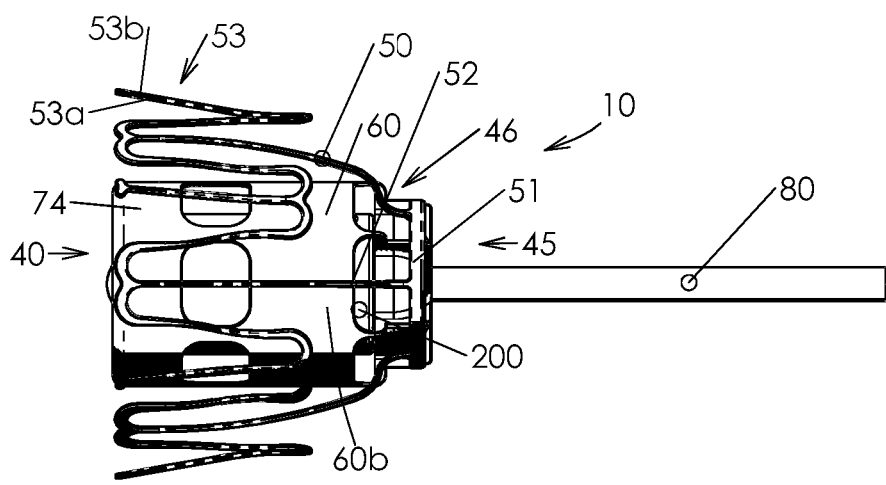

FIG. 4A-4B are side views of the device according to the exemplary embodiment of FIG. 1. FIG. 4A depicts the anchor in the collapsed configuration, and FIG. 4B depicts the anchor in the expanded configuration.

Figure 5A:
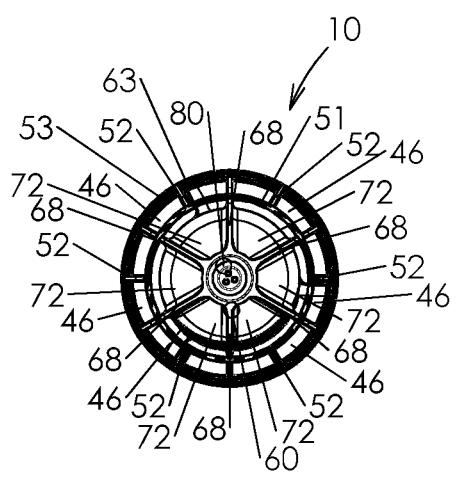
Figure 5B:
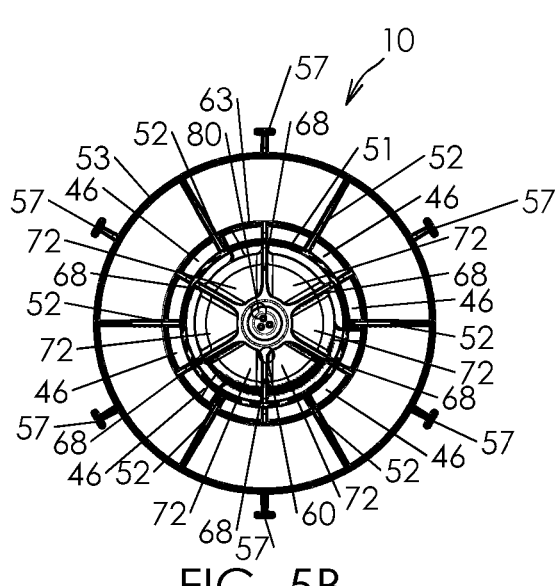

FIG. 5A-5B are proximal axial views of the device according to the exemplary embodiment of FIG. 1. FIG. 5A depicts the anchor in the collapsed configuration, and FIG. 5B depicts the anchor in the expanded configuration.

Figure 6A:
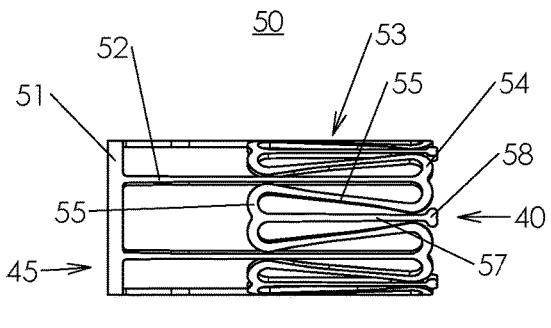
Figure 6B:
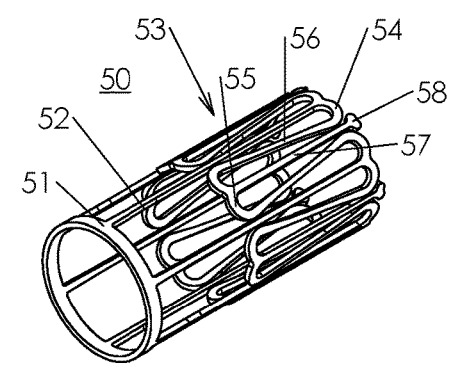

FIG. 6A-6B are views of the anchor as laser cut from a tubular structure according to the exemplary embodiment. FIG. 6A is a side view, and FIG. 6B is a proximal perspective view.

Figure 7A:
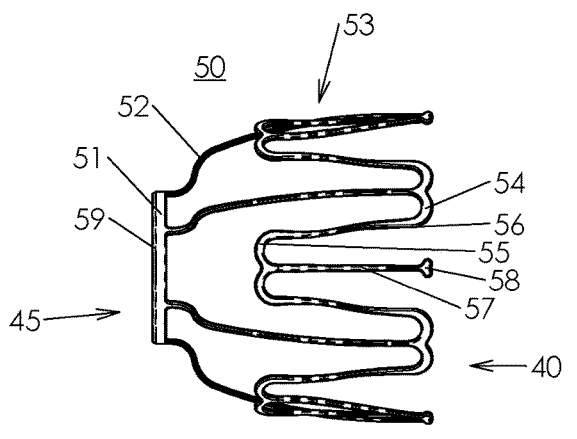
Figure 7B:
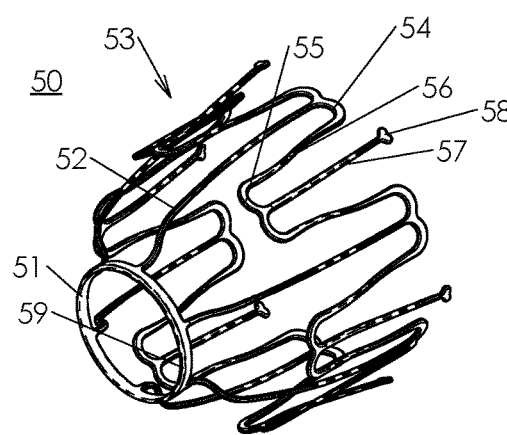

FIG. 7A-7B are views of the anchor as finished in the expanded configuration according to the exemplary embodiment. FIG. 7A is a side view, and FIG. 7B is a proximal perspective view.

FIG. 8A-8D are views of a frame of the device according to the exemplary embodiment. FIG. 8A is a distal perspective view, FIG. 8B is a proximal perspective view, FIG. 8C is a proximal axial view, and FIG. 8D a sectional view of the frame taken along line 8D in FIG. 8C.

Figure 9A:
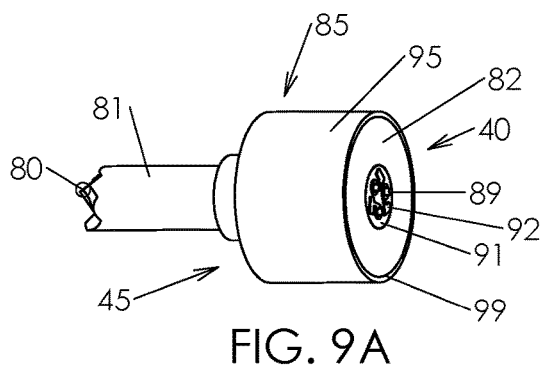
Figure 9B:
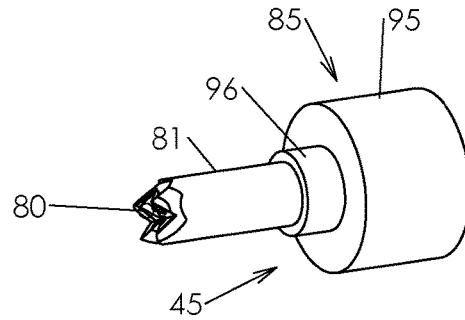
Figure 9C:
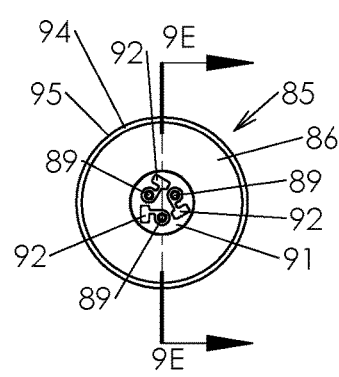
Figure 9D:
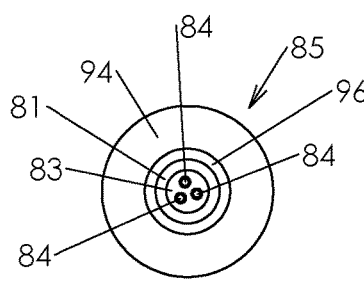
Figure 9E:
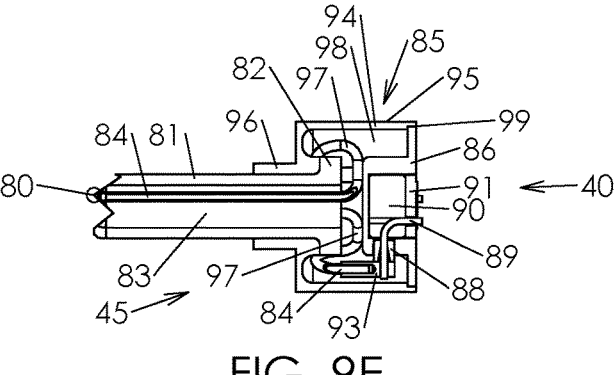

FIG. 9A-9E are views of a feedthrough assembly according to the exemplary embodiment of the present invention. FIG. 9A is a distal perspective view, FIG. 9B is a proximal perspective view, FIG. 9C is distal axial view, FIG. 9D is a proximal axial view, and FIG. 9E is a sectional view along the line 9E of FIG. 9C.

Figure 10A:
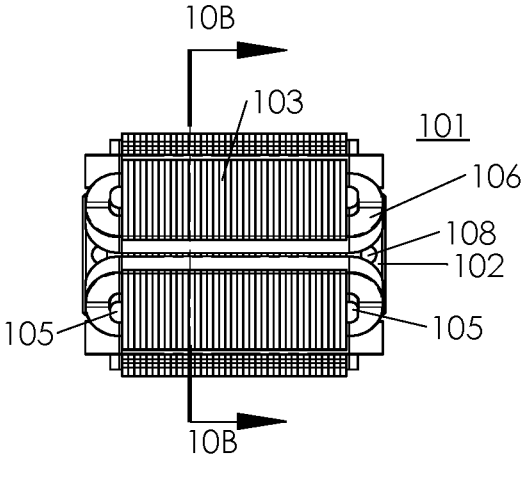
Figure 10B:
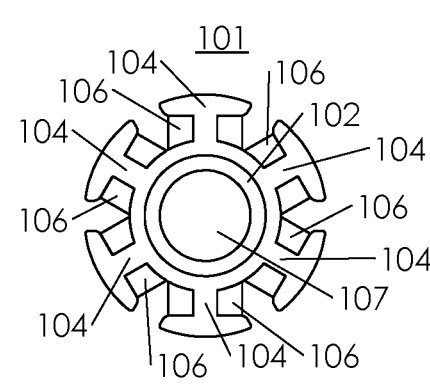
Figure 10C:
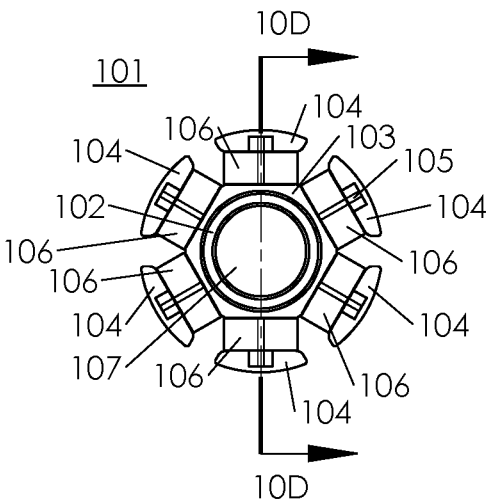
Figure 10D:
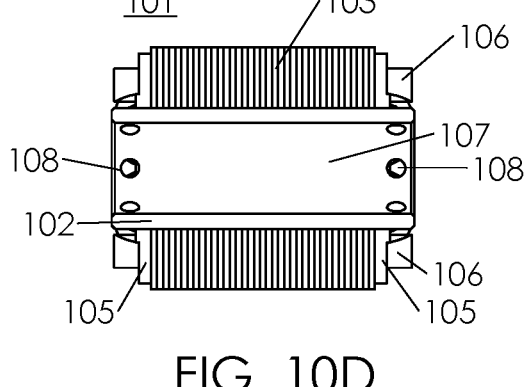

FIG. 10A-10D are views of a motor stator of the device according to the exemplary embodiment. FIG. 10A is side view, FIG. 10B is an axial sectional view taken along the line 10B of FIG. 10A, FIG. 10C is an axial view, and FIG. 10D is a sectional view taken along the line 10D shown in FIG. 10C.

Figure 11A:
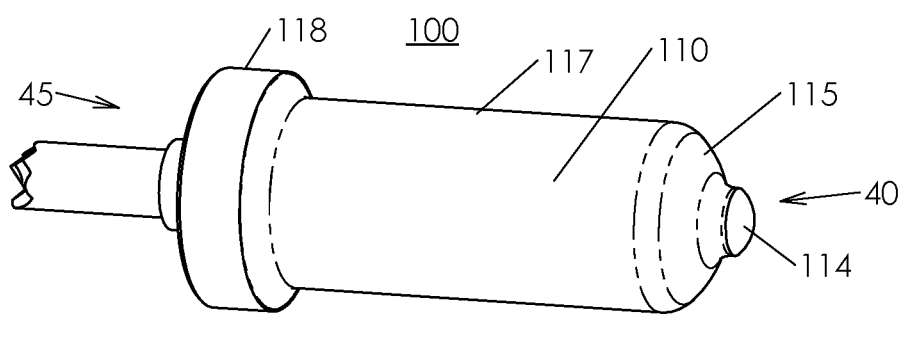
Figure 11B:
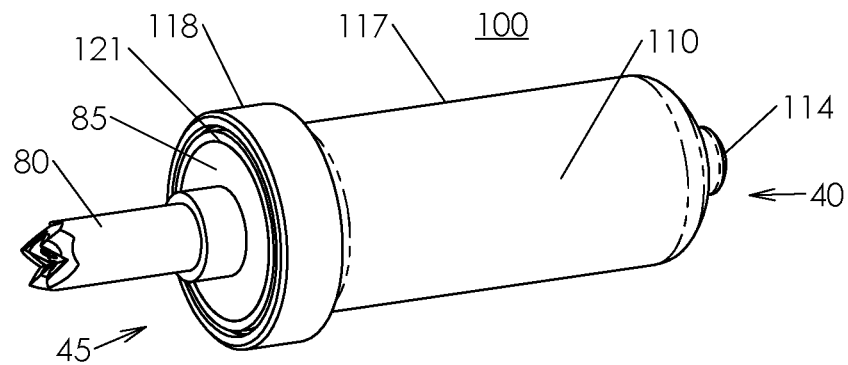
Figure 11C:
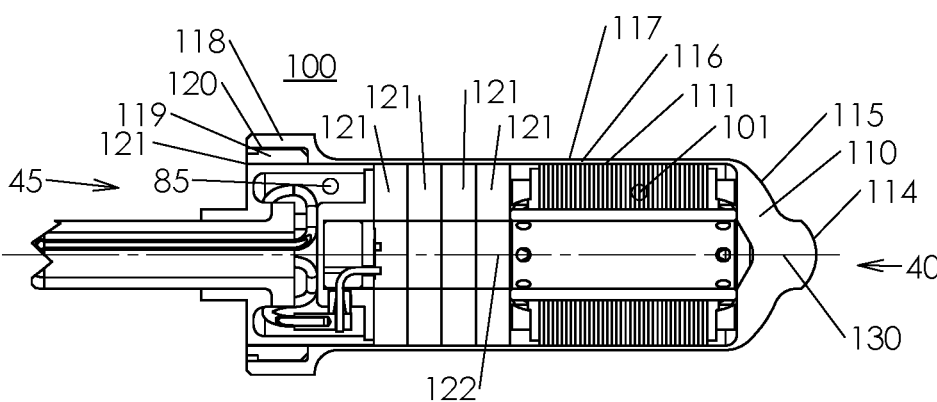

FIG. 11A-11C are views of a stator housing assembly of the device according to the exemplary embodiment of FIG. 1. FIG. 11A is a distal perspective view, FIG. 11B is a proximal perspective view, and FIG. 11C is a mid-plane sectional view taken along longitudinal axis of the stator housing assembly of FIG. 11B.

Figures 12A, 12B:
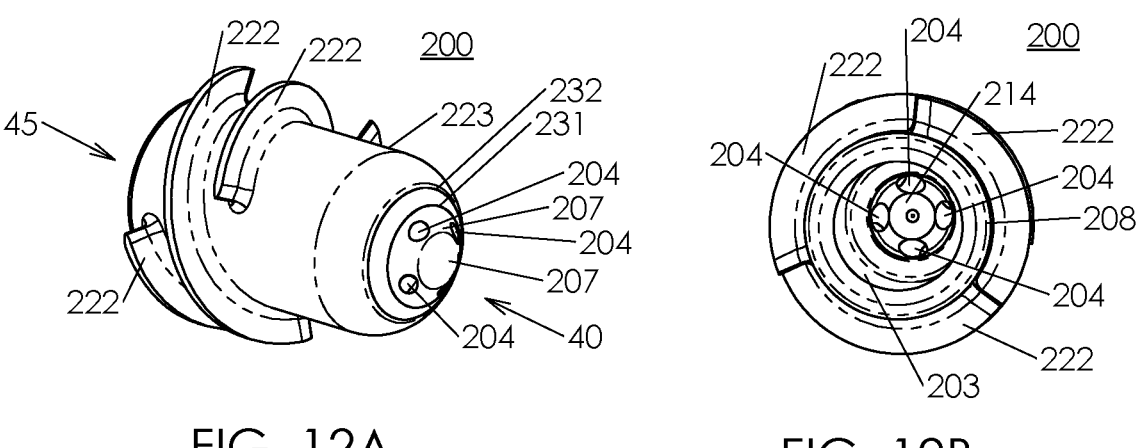
Figure 12C:
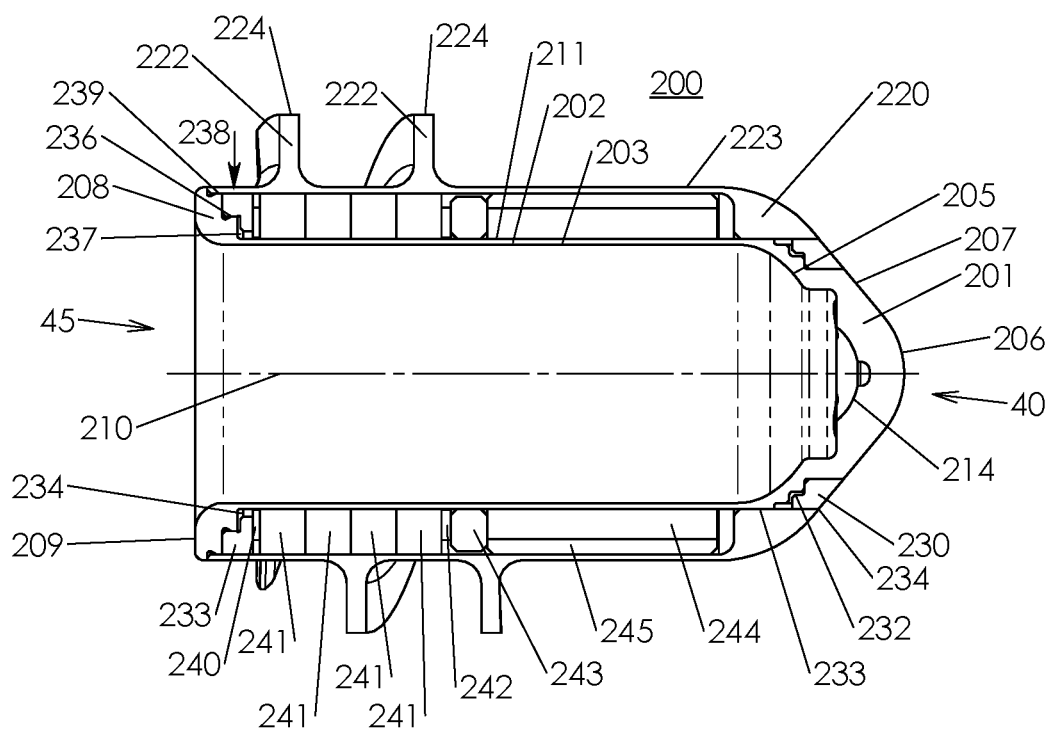

FIG. 12A-12C are views of a rotor housing assembly of the device according to the exemplary embodiment of FIG. 1. FIG. 12A is a distal perspective view, FIG. 12B is a proximal perspective view, and FIG. 12C is mid-plane sectional view taken along a longitudinal axis of the rotor housing assembly of FIG. 12A.

Figure 13:
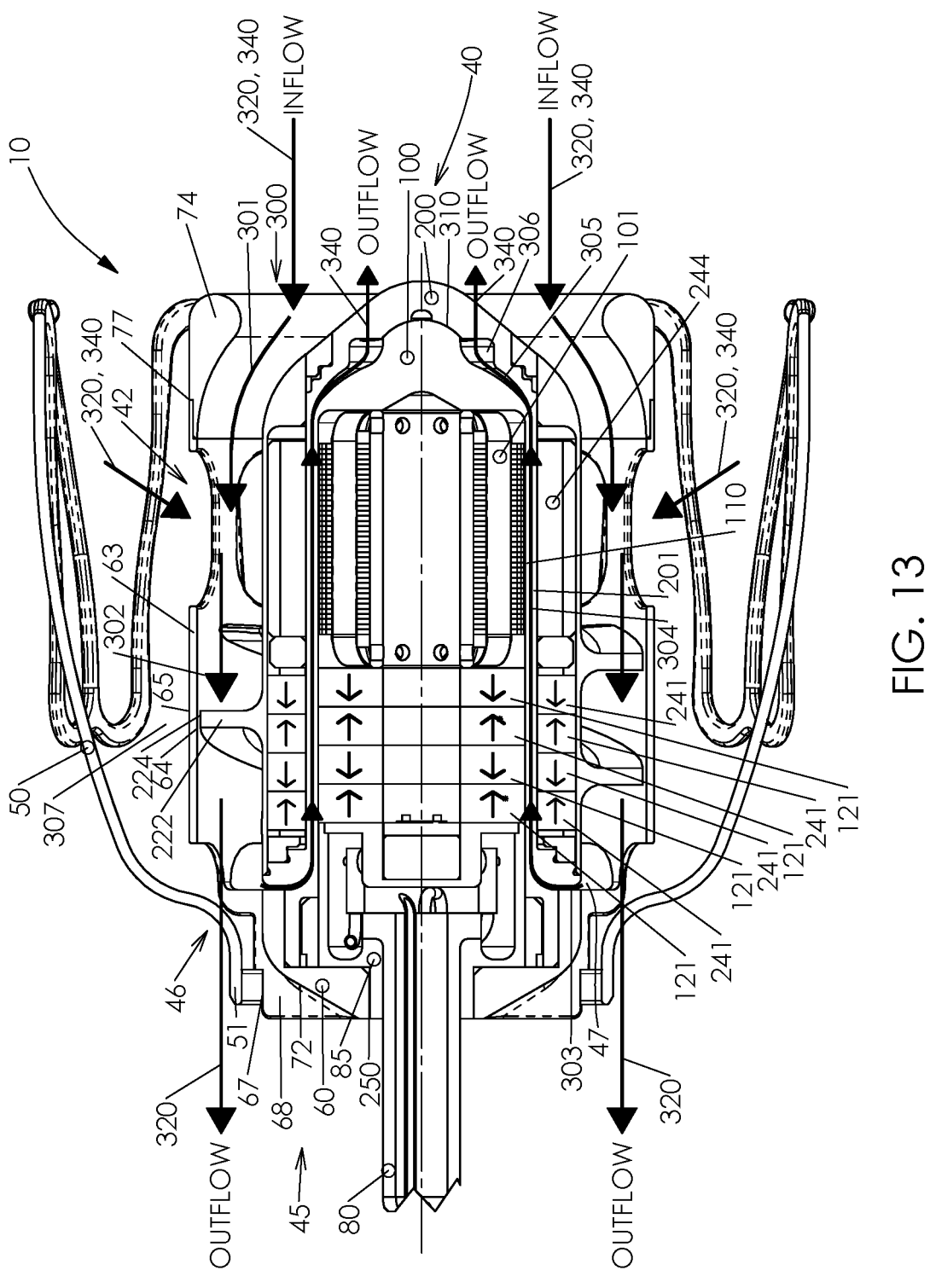

FIG. 13 is an enlarged mid-plane sectional view of the device of FIG. 1 according to the exemplary embodiment.

Figure 14:
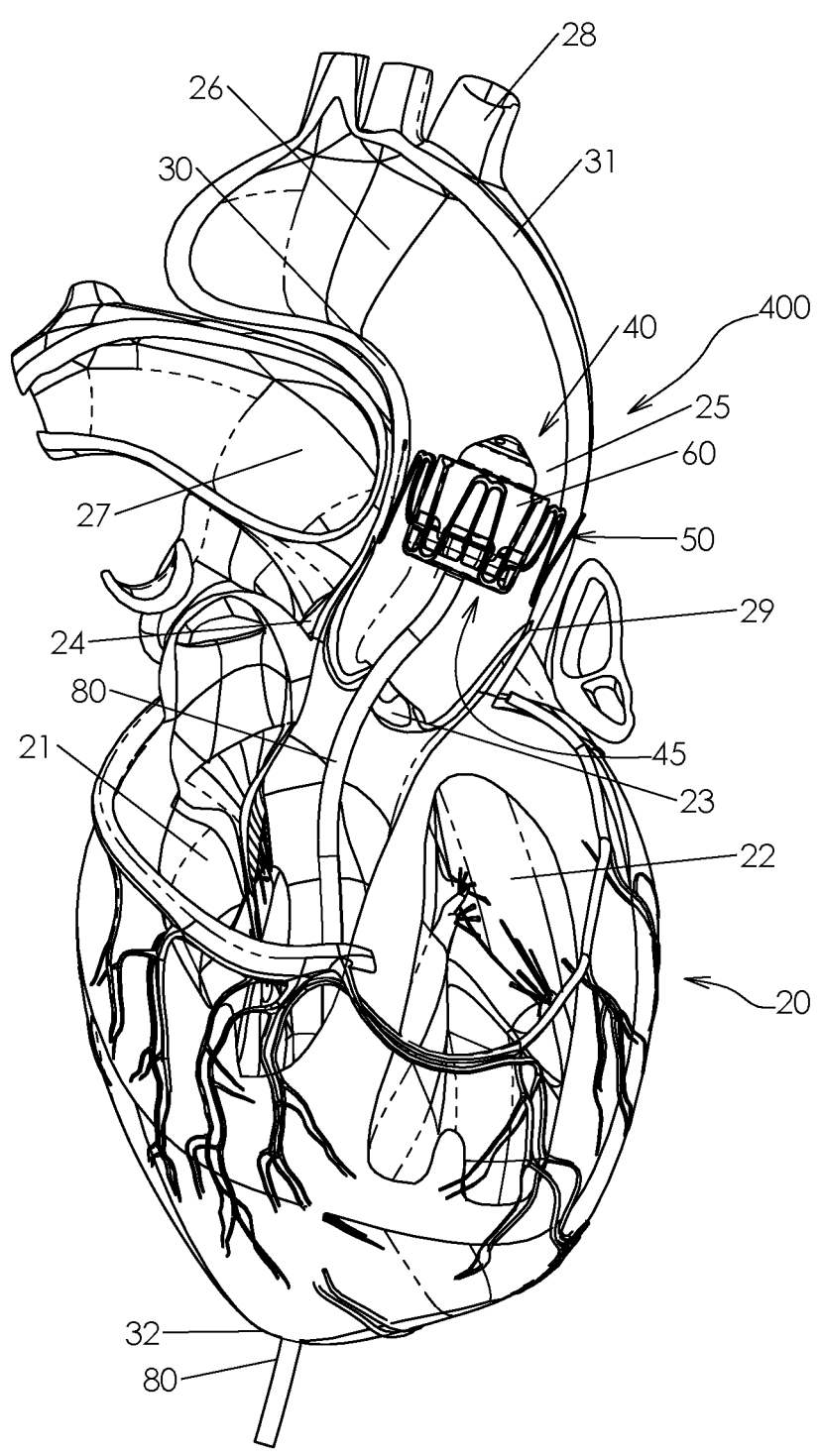

FIG. 14 is a sectioned posterior view of a human heart with an alternative exemplary embodiment of a ventricular assist device of the present disclosure depicted in an approximate relative position within an ascending aorta and other surrounding anatomy.

Figure 15:
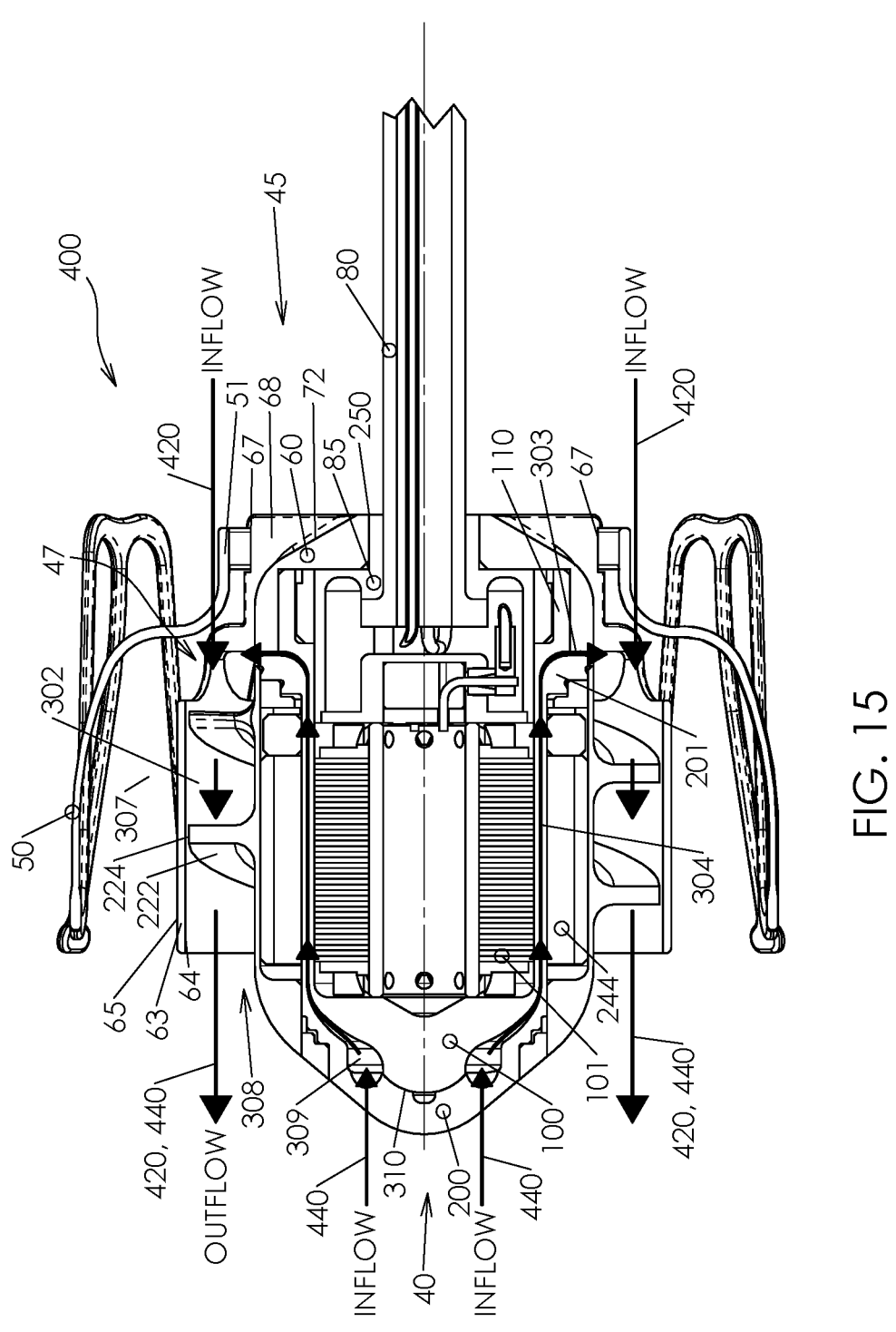

FIG. 15 is an enlarged mid-plane sectional view of the device of FIG. 14 according to the alternative exemplary embodiment.

DETAILED DESCRIPTION

Before describing exemplary embodiments, it is noted that the embodiments reside primarily in combinations of apparatus components related to an extravascular cuff with lateral restraints. Accordingly, ventricular device and method components have been represented where appropriate by conventional symbols in the drawings, showing only those specific details that are pertinent to understanding the embodiments of the present disclosure. As a result, details that will be readily apparent to those of ordinary skill in the art having the benefit of the foregoing description are not necessary to include.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with", "coupled to" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

Referring now to FIG. 1, a ventricular assist device 10 according to an exemplary embodiment of the present disclosure is depicted. The ventricular assist device 10 is depicted according to an exemplary embodiment in context with a posterior sectioned illustration of a human heart 20. For reference, anatomical features of the human heart 20 include a left ventricle 21, a right ventricle 22, an aortic valve 23, a coronary artery 24, an ascending aorta 25, an aortic arch 26, a pulmonary artery 27, a brachiocephalic artery 28, an aortic root 29, a lesser curve 30, and a greater curve 31. The device 10 comprises a distal end 40 and a proximal end 45 with a lead 80 extending from proximal end

45. The device 10 is an axial elongated structure sized to within a blood vessel such as the ascending aorta (shown in FIG. 1). The ventricular assist device 10 includes a frame 60 with an anchor 50 affixed thereto. The anchor 50 is adapted for contacting and supporting the device in a selected location within an artery and also includes a distal end 40 and a proximal end 45. In this example, the distal end 40 of the anchor 50 is disposed near the aortic root 29 in relatively close proximity to the aortic valve 23, but also downstream from the coronary artery 24. The ventricular assist device 10 augments blood flow by pumping blood received near the distal end 40 and ejected near the proximal end 45, as explained more below. In addition to blood flowing through the device, blood can also flow in the annular space around the outside of frame 60 to bypass the pump mechanism within the frame 60.

In further reference to FIG. 1, the anchor 50 is constrained in a collapsed configuration and is placed through an incision in the greater curve 31 and positioned within the ascending aorta 25. The anchor 50 is then allowed to expand to hold the device 10 to the ascending aorta 25 in the approximate position indicated. Accordingly, the device 10 is positioned upstream from aortic arch 26 at a relatively straight luminal position of ascending aorta 25 prior to curvature associated with the lesser curve 30 and the greater curve 31. Although the lead 80 is shown coaxial with the device 10, the lead 80 is flexible and would be bent within the ascending aorta 25 to exit normal to the aortic wall along greater curve 31.

In addition, the lead 80 is of a sufficient length (full length not shown) to extend to a controller 12 that provides power to the ventricular assist device 10 and controls an operational speed of a rotor assembly of the device 10, as explained more below. More specifically, the controller 12 includes a power source 12A and a timing control module 12B, both of which are operatively coupled to the rotor assembly, and the controller is programmed to operate the power source to provide a pulsatile flow. In response to application of power, such as electrical power, from the controller 12 (and/or the power source 12A) to a stator assembly, the rotor assembly rotates about its axis to move blood through the device 10 along designated flow paths, as also explained more below. The controller 12 may be located inside or outside the patient's body. Preferably, the controller may be coupled to an ECG lead, an ECG sensor, and/or alternative sensing means 13, such as a pressure sensor, to monitor the cardiac cycle for the purposes of modulating the rotor rotational speed and providing a pulsatile output modulated in synchronization with the heart rhythm. In one example, the sensor 13 is arranged to sense native cardiac rhythms and is operatively coupled to the timing control module 12B of the control system 12. In one form, the timing control module 12B is arranged to control the rotational speed of the rotor assembly between a baseline speed and a higher speed. The baseline speed may be zero, or non-zero. There may be power-saving advantages to maintaining the baseline speed as a non-zero speed. When the rotor assembly is at or near the baseline speed, the rotor assembly may effectively function as a closed valve. On the other hand, at the higher speed, the rotor assembly is arranged to move blood along a flow path at a desired rate.

Referring now to FIGS. 2-5, the ventricular assist device 10 of the exemplary embodiment is depicted without reference to an interfacing blood vessel. FIGS. 2-5 designated with "A" depict the anchor 50 of device 10 in a collapsed configuration with an annular brace portion against an outer surface of the frame 60 as is exemplary for delivery within the vessel. FIGS. 2-5 designated with "B" depict the anchor 50 of the device 10 in a fully expanded configuration with the annular brace portion offset outward from frame 60. When engaged with the inner surface of a luminal blood vessel, anchor 50 will assume some intermediate state between the collapsed and fully expanded configurations shown depending on the size and mechanical properties of the blood vessel.

Referring now to FIGS. 2A and 2B, the anchor 50 is a stent-like structure affixed to proximal end 45 of frame 60 and includes an annular base 51, a strut 52, and an annular brace portion 53 that is adapted to support the device 10 within a luminal structure, such as the aorta or pulmonary artery. Also depicted is the frame 60, a guard 74 attached to the distal end of the frame 60, and a rotor assembly 200 disposed within the frame 60. The frame 60 includes a plurality of fenestrations 66 disposed near the distal end 40 of the frame 60, and the rotor assembly 200 includes a plurality of through-holes 204 The guard 74 is located at the distal end 40 and is affixed to the frame 60 to provide an atraumatic distal structure for abutting against surrounding soft tissue and preventing contact with the rotor assembly 200 as it spins.

As the rotor enclosure assembly 200 rotates at high speed, blood is drawn into frame 60 from an annular inlet 300 and into the plurality of fenestrations 66 of frame 60. In addition, while blood primarily exits the device 10 at the proximal end 45 of the frame 60, a minor amount of blood will exit through the plurality of through-holes 204 in the rotor assembly 200, as explained more below. This is to provide washing through a fluid gap between a stator assembly and rotor enclosure assembly 200, which is not depicted in these figures, but is also explained more below. Referring now to FIGS. 3A and 3B, the device 10 also includes a plurality of outlet slots 46 disposed at the proximal end 45 and through which blood primarily exits. The device 10 pumps blood out of outlet slot(s) 46 as defined by the frame 60 at elevated pressure for augmenting blood flow provided by the heart. As further depicted, the frame 60 also includes a plurality of proximal projections 68 disposed at the proximal end 45 and a plurality of diffuser zones 72. As blood exits the plurality of outlet slot(s) 46, the blood travels between the plurality of proximal projection(s) 68 and through the plurality of diffuser zone(s) 72 before moving further downstream from the proximal end 45. The presence of the annular base 51 of the anchor 50 directly in the outflow path serves to reduce the risk of thrombosis near the interface between the frame 60 and the anchor 50, and along the sides of proximal projection(s) 68 that are adapted to support annular base 51 of anchor 50 and for fixation of the anchor 50 to the frame 60.

Referring now to FIGS. 4A-4B, the device 10 is depicted with the anchor 50 in a collapsed configuration in FIG. 4A, and the anchor 50 is in an expanded configuration in FIG. 4B. More specifically, the device 10 includes the frame 60 with the distal end 40 and the proximal end 45, and the anchor 50 having an annular brace 51 attached to the proximal end 45 of the frame 60. The frame 60 also includes an outer surface 60b, which contacts a portion of the anchor 50, as explained more below. The annular brace 53 is coupled to the annular brace 51 and includes an inner surface 53a and an outer surface 53b, and the outer surface 53b is sized for placement within a blood vessel or an artery. The lead 80 is depicted extending from the proximal end 45 of the frame 60 and is operatively coupled to a power source (not depicted). The anchor 50 is moveable between the collapsed configuration of FIG. 4A, in which the inner surface 53a contacts the outer surface 60b of the frame 60, and the expanded configuration. The expanded configuration is a configuration in which the inner surface 53*a* of the anchor 50 is offset from the outer surface 60*b* of the frame 60, and the outer surface 53*b* engages a portion of the blood vessel (not shown) to secure the frame 60 within the blood vessel.

Referring now to FIGS. 5A and 5B, proximal axial views of the device 10 are depicted with the anchor 50 in the collapsed configuration in FIG. 5A, and the anchor 50 in the expanded configuration in FIG. 5B. As depicted therein, the plurality of proximal projections 68 of the frame 60 extend around a circumference of the frame 60, and each proximal projection 68 is equidistantly spaced from another proximal projection 68. In this example, there are six proximal projections 68, but it will be understood that there may be more or fewer proximal projections 68 in the plurality of projections 68 and still fall within the scope of the present disclosure. In a similar manner, the plurality of diffuser zones 72 is also depicted, and each diffuser zone of the plurality of diffuser zones is disposed between each proximal projection of the plurality of projections and around the circumference of the frame 60. Like the plurality of proximal projections 68 of the frame 60, the plurality of diffuser zones 72 includes six diffuser zones in this example, but there may be more or fewer diffuser zones 72 of the plurality of diffuser zones and still fall within the scope of the present disclosure.

As further depicted, the plurality of proximal projection(s) 68 are engaged with annular base 51 of anchor 50, and ideally each strut 52 of the anchor 50 is positioned in a centralized position with respect to the plurality proximal projection(s) 68. Correspondingly, in this example, there are also six outlet slot(s) 46 of the plurality of outlet slots 56 through which blood exits the device 10. As will be appreciated, there may be more or fewer outlet slots 46 and still fall within the scope of the present disclosure. Exiting blood flows between the plurality of outlet slot(s) 46 and along the plurality of diffuser zone(s) 72. Also depicted is a plurality of prongs 57 integrated with the annular brace 53 to facilitate anchoring of the anchor 50 within lumen of artery or another vessel, as explained more below. The prongs 57 are biased outward for retention when engaging soft tissue.

Referring now to FIGS. 6A-6B and 7A-7B, the anchor 50 according to the present invention is depicted as laser cut from tubing prior to being further processed to exhibit a finished configuration in FIGS. 6A-6B In FIGS. 7A-7B, the anchor 50 is depicted after finishing and shape setting in an expanded configuration. The anchor 50 is preferably a shape-settable Ni—Ti super elastic alloy known as nitinol and is laser cut from a nitinol tube, having an outer diameter OD of approximately 15 mm. After the laser cutting processing, the anchor 50 is subjected to finishing operations to achieve the configuration shown in FIGS. 7A-7B. These finishing operations include adding a chamfer 59 to the annular base 51, electropolishing to achieve rounded corners and edges, and shape setting the nitinol in to the expanded configuration shown by heat treatment of the anchor 50 in an oven under a controlled thermal conditioning cycle, for example. Of course, various other known finishing operations may alternatively and/or additionally be used and still fall within the scope of the present disclosure.

As depicted in FIGS. 6A-6B and 7A-7B, the anchor 50 comprises the annular base 51 at the proximal end 45. Extending from annular base 51 is at least one strut 52, and in this example a plurality of struts 52, which serve as a flexible coupling between the annular base 51 and the annular brace portion 53 at the distal end 40. The annular brace portion 53 is the tissue interfacing portion of the anchor 50 and comprises a plurality of distal junction(s) 54, a plurality of cross beam(s) 56 and a plurality of proximal junction(s) 55 to form a continuous zig-zag structure. Centered along occurrences of proximal junction(s) 55 are the plurality of prong(s) 57 to further support the anchor 50 within the lumen of a vessel and to help resist migration of the device 10 away from an initial position at implant. At the distal end 40 of each prong of the plurality of prongs 57 is a prong tip(s) 58 to distribute pressure and not cause excessive stress concentration to vessel that is engaged.

The geometry of strut 52, the plurality of distal junction(s) 54, the plurality of proximal junction(s) 55, the plurality of cross beam(s) 56, and the plurality of prong(s) 57 is optimized for sufficient stiffness to anchor the device 10 within vessel, but not to be overly stiff and non-compliant to the extent that would cause erosion or other damage to the blood vessel near any contacting surfaces. In this example, the annular brace portion 53 of the anchor 50 is expanded from a minimum outer diameter OD of about 15 mm to a maximum outer diameter OD of approximately 30 mm, e.g., in the expanded configuration. When the annular brace 53 is supported within the lumen of a blood vessel, the annular brace 53 will deflect inward and exhibit a smaller outer diameter OD due to reaction forces applied to the annular brace 53 by the blood vessel inner surface, for example.

Referring now to FIGS. 8A-8D, the frame 60 and the guard 74 of the device 10 are depicted. The frame 60 is a structural element that supports an internal pump mechanism along a feedthrough bore 61 and a stator bore 62 near the proximal end 45. At the proximal end 45, and as previously noted, the frame 60 includes the plurality of proximal projection(s) 68 separated by outlet slots (s) 69 and diffuser zone(s) 72. Each proximal projection of the plurality of proximal projection(s) 68 includes a proximal slot(s) 67 for interfacing with the anchor 50 (not shown). The frame 60 is further characterized with a proximal outer surface 70 and a proximal shoulder 71 along transition to a shroud 63. The shroud 63 is of a thin wall thickness and comprises shroud inner surface 64 defining a portion of a flow path and a shroud external surface 65. As noted, the distal end 40 of the frame 60 includes a plurality of distal fenestrations 66, which are also depicted in FIGS. 8A-8D The proximal outer surface 70 includes a diameter less than a diameter of the shroud external surface 65, which best ensures washing along the proximal outer surface 70. In addition, the proximal outer surface 70 has a diameter that is approximately the same as the outer diameter OD of the annular base 51 of the anchor 50. At the distal end 40, the frame 60 includes a guard interface 73 for attachment to the guard 74. The guard 74 includes a distal lip 75, an expansion zone 76, a seam 77, and an outer surface 78. The outer surface 78 has approximately the same outer diameter OD as the outer diameter of the shroud external surface 65. Further, the guard 74 is preferably welded to the frame 60 along a seam 77. The distal lip 75, the expansion zone 76, and the shroud inner surface 64 together define a primary stationary interior flow surfaces of the pump mechanism according to the present invention.

Referring now to FIGS. 9A-9E, a feedthrough assembly 85 of the ventricular assist device 10 is shown according to the exemplary embodiment. The feedthrough assembly 85 incorporates the lead 80 projecting outward from the proximal end 45. The lead 80 is a flexible cable comprising a jacket 81 and a multi lumen extrusion 83 for incorporating a plurality of wire conductor(s) 84 therein for providing power to the device. In one example, the plurality of wire conductors 84 includes three wire conductors, but more or fewer wire conductors may be included and still fall within the scope of the present disclosure. Towards the distal end 40, the jacket 81 includes the flange 82 for engagement and retention within the feedthrough cover 94. The feedthrough assembly 85 includes the enclosure elements of a feedthrough flange 86 and a feedthrough cover 94 within a small volume. Within this space are the terminations of the plurality of wire conductor(s) 84 to a plurality of feedthrough pin(s) 89. Accordingly, an insulated electrical path is provided for the plurality of feedthrough pin(s) 89 through the plurality of insulator(s) 88 seated within a radial wall of the feedthrough flange 86 in three radial positions 120 degrees apart. More generally, each insulator of the plurality of insulators 88 is disposed equidistantly from another insulator of the plurality of insulators. While three feedthrough pins and three insulators are included in one example of the plurality of feedthrough pin(s) 89 and insulators 88, it is understood that more or fewer feedthrough pins and insulators many alternatively be used and still fall within the scope of the present disclosure.

In addition, the plurality of insulator(s) 88 are brazed to the feedthrough flange 86 and the plurality of feedthrough pin(s) 89 are brazed within the plurality of insulator(s) 88. The plurality of feedthrough pin(s) 89 are bent to transition pins from a radial projection to an axial projection. Further, the spacer 90 helps ensure this axial orientation of the plurality of feedthrough pin(s) 89 while also providing an end surface near the distal end 40 for supporting a printed circuit board 91 within a counterbore of the feedthrough flange 86.

As best depicted in FIG. 9C, the printed circuit board 91 includes a plurality of pcb trace(s) 92 that define an electrically conductive path from the plurality of feedthrough pin(s) 89 to solder pads. This configuration provides solder pads for soldering magnet wire thereto, which is routed from a motor stator, for example.

Referring now to FIG. 9E, the plurality of wire conductor(s) 84 are preferably a stranded cable made of MP35N tubes that are filled with silver. For each wire conductor(s) 84 of the plurality of wire conductors 84, numerous silver-filled tubes are stranded together, and a layer of insulation material is added to the stranded wires. This technology is known as DFT wire that is manufactured by Fort Wayne Metals in Fort Wayne, Indiana. The composite structure of DFT wire enables strength and fatigue resistance while also exhibiting acceptable conductivity through the length of the lead 80. As is standard practice in the art of hermetic feedthroughs, instances of feedthrough pin(s) 89 are preferably 80% platinum, 20% iridium or some alternative alloy with acceptable corrosion resistance and biocompatibility. To terminate the plurality of wire conductor(s) 84 to the plurality of feedthrough pin(s) 89, a plurality of crimp ferrule(s) 93, made from a Platinum Iridium alloy, are crimped on the distal ends of the plurality of wire conductor(s) 84. Thus, the plurality of crimp ferrule(s) 93 can be laser welded over a portion of each feedthrough pin of the plurality of feedthrough pin(s) 89 to ensure a welded electrical connection between the respective plurality of wire conductor(s) 84 and the plurality of feedthrough pin(s) 89. The feedthrough cover 94 is joined to the feedthrough flange 86 and is preferably laser welded at a seam 99. Together the feedthrough cover 94 and the feedthrough flange 86 define a cavity 98, which incorporates sufficient space to facilitate a plurality of wire loop(s) 97. After assembly of the feedthrough cover 94 to the feedthrough flange 86, the cavity 98 can be epoxy filled to secure wire loop(s) 97 in position. This provides sufficient strain relief to isolate terminations from any axial tension that may be applied through the plurality of wire conductor(s) 84.

Referring now to FIG. 9E, the flange 82 of the cable jacket 81 is captured into the collar portion 96 and, thus, the jacket 81 is prevented from migrating out of the feedthrough assembly 85. The feedthrough cover 94 further includes a collar portion 96 to provide additional overlap of the jacket 81 and for defining a weld seam with the frame 60. The feedthrough assembly 85 includes an outer surface 95 for interfacing with the stator enclosure assembly according to the present invention as will be described in reference to additional figures. The primary objectives with respect to the feedthrough assembly 85 are to provide a hermetic feedthrough, to structurally isolate the cable terminations, and to anchor the jacket 81 of the lead 80 within as small of a volume as possible. According to this example, the feedthrough assembly 85 has an outer diameter OD of approximately 8 mm and an axial length of approximately 7.6 mm. The lead 80 is preferably characterized by an outer diameter OD of 3 mm or less.

Referring now to FIGS. 10A-10D, a motor stator assembly 101 of the device 10 according to the exemplary embodiment is depicted. In this preferred embodiment the motor stator assembly 101 fits within a volume corresponding to an 8 mm outer diameter OD and a length of 10 mm. The motor stator assembly 101 is a brushless DC (BLDC) motor with 6 windings and three phases. The motor stator assembly 101 includes a plurality of lamination(s) 103 stacked upon and bonded to each-other. The plurality of lamination(s) 103 are preferably assembled over the support tube 102 in a centralized position. An end spacer 105 is provided at each end to enable the plurality of winding(s) 106 to be wrapped around end faces of a stack of multiple lamination(s) 103 so as to not abrade the numerous turns of magnet wire. Each lamination(s) 103 comprises at least one lamination tooth 104 for wrapping each winding 106 of the plurality of windings. In addition, each winding(s) 106 represents numerous layers and turns of a small diameter magnet wire. For example, one winding(s) 106 of the plurality of windings 106 may comprise thirty or more loops of magnet wire. The plurality of winding(s) 106 may be terminated in a configuration as is commonly practiced for BLDC motors. The support tube 102 includes bore 107 and a plurality of side hole(s) 108 at each end. These allow the terminations of magnet wire to be fed through into bore 107 without obstructing the ends of the support tube 102.

Referring now to FIGS. 11A-11C, a stator assembly 100 according to the exemplary embodiment is depicted. The stator assembly 100 includes a stator housing 110, which is preferably made from a zirconia ceramic material such as TZP-A. Such a ceramic material is highly biocompatible, non-thrombogenic and wear resistant. Additionally, advanced ceramics have high hardness and can be machined to high precision tolerances to within several micrometers. Additionally, the stator housing 110 is not electrically conductive and thus eddy currents will not be induced in a sleeve portion 116 of the stator housing 110 as rotor enclosure assembly 200 rotates about axis 130. The stator housing 110 includes a convex thrust bearing surface 114 at the distal end 40, which serves a part of a wear resistant thrust bearing. Additionally, the stator housing 110 includes an expansion surface 115, a sleeve outer surface 117, and a flange portion 118 at the proximal end 45. As depicted in FIG. 11C, the stator housing 110 is an elongated hollow structure with the sleeve portion 116 over the majority of its length defined. The thickness of sleeve portion 116 is approximately 0.2 mm. The stator housing 110 includes a stator housing bore 111 that is open at one end for insertion and accommodation of internal components. Prior to assembly of the internal components, a ring 119 is brazed to the stator housing 110 along braze joint 120. The ring 119 is preferably titanium, and the braze joint 120 disposed between the flange portion 118 and the ring 119 is preferably gold. In the respective order of assembly of components through the stator housing bore 111, the stator housing 110 receives the motor stator assembly 101, a plurality of stator bearing magnet(s) 121, and a feedthrough assembly 85. A plurality of magnet wires of motor stator assembly 101 (not shown) are routed through a cavity 122 and terminated to pcb trace(s) 92 of the feedthrough assembly 85 prior to complete insertion of the feedthrough assembly 85. Finally, the feedthrough assembly 85 is welded to the ring 119 at the weld seam 121.

The configuration of the stator assembly 100 described above enables an elongated component stator housing 110 including both the convex thrust bearing surface 114 and the sleeve portion 116 to be made from a durable zirconia ceramic material, while also achieving a hermetically sealed assembly in internal components. Such internal components include the motor stator assembly 101 and the plurality of stator bearing magnet(s) 121 that are sealed off from external fluid and gases. By integrating the convex thrust bearing surface 114 as part of the same component comprising the sleeve 116, the stator assembly 100 can be made of a reduced overall length as compared to if the convex thrust bearing surface 114 was implemented in a separate interfacing component, for example.

Referring now to FIGS. 12A-12C, a rotor assembly 200 according to the exemplary embodiment is depicted. The rotor assembly 200 includes a rotor housing 201 having a hollow elongate structure open at proximal end 45. The rotor housing 201 includes a nose portion 206 externally at the distal end 40. Internally, the rotor housing 201 includes an internal expansion zone 205 that transitions to a sleeve portion 202, which is characteristic over most of the length of sleeve portion 202. The rotor housing 201 also includes a proximal flange 208 at the proximal end 45. The rotor housing 201 is preferably made of a Zirconia ceramic similar to the material described above for the stator housing 110, with the thickness of the sleeve portion 202 being approximately 0.2 mm. Thus, the concave thrust bearing surface 214, which needs to be implemented on a wear resistant bearing material, is integrated in the same component incorporating the sleeve portion 202. Implementing the concave thrust bearing surface 214 as a feature of the rotor housing 201 and not in a separate interfacing component enables the overall length of the ventricular assist device 10 to be kept at a minimum. Outside surfaces of rotor housing 201 at the distal end 40 include the nose portion 206 and a conical surface 207. As depicted in FIGS. 12A-12B and noted above, the rotor housing 201 also includes a plurality of through hole(s) 204 for allowing blood flow through the distal end 40 of the rotor housing 201. In this example, the plurality of through-holes 204 includes four through-holes, but more or fewer through-holes may alternatively be used and still fall within the scope of the present disclosure. Each through-hole of the plurality of through hole(s) 204 is axially offset outside of concave thrust bearing surface 214 and is canted relative to a rotational axis 210 (not parallel with respect to axis 210) of the rotor assembly 200

As part of a sub-assembly of the rotor assembly 200, a distal braze ring 230 is brazed to the rotor housing 201 at the distal end 40 along a distal braze joint 232. A proximal braze ring 235 is brazed to the rotor housing 201 along a proximal braze joint 237. Preferably, the distal braze ring 230 and the proximal braze ring 235 are made from titanium or titanium alloy and a braze used to join with the rotor housing 201 is gold. The distal braze ring 230 includes an external surface with is substantially coincident with the conical surface 207 of the rotor housing 201. Before attachment and joining of the impeller shell 220, several components are inserted over a sleeve outer diameter OD 211 of the rotor housing 201 from the distal end 40, which abut against the proximal braze ring 235. Such components may include one or more of a rotor bearing shim 240, a plurality of rotor bearing magnet(s) 241, such as four rotor bearing magnets, a rotor motor shim 242, a rotor motor spacer 243, and a plurality of rotor motor magnet(s) 244 assembled within a rotor motor back iron 245. As depicted in FIG. 13, the rotor bearing shim 240, the rotor motor shim 242, and the rotor motor spacer 243 are sized in axial length to ensure optimal alignment of instances of the plurality of rotor bearing magnet(s) 241 and the plurality of rotor motor magnet(s) 244 with respect to stator components pertaining to the motor stator and internal bearing magnets. The plurality of rotor bearing magnets (s) 241 and the plurality of rotor motor magnet(s) 244 are preferably bonded to the sleeve outer diameter OD 211 of the rotor housing 201 using a suitable epoxy.

The rotor assembly 200 further includes an impeller shell 220, which provides an exterior cover of the components mentioned above. The impeller shell 220 is preferably made with a titanium alloy and fits over the distal end 40 of the rotor housing 201 along a proximal impeller shell interface 239 and the distal end 40 of the rotor housing 201 along the sleeve outer diameter OD 211. The impeller shell 220 includes an impeller hub outer surface 223 disposed near the distal end 40 and a plurality of blade tip surfaces 224 near the proximal end 45. The impeller shell 220 is welded to the distal braze ring 230 along a distal weld seam 234 near the distal end 40 and is welded to a distal impeller shell interface 233 at an approximated position of a proximal weld joint 238. Accordingly, the finished sub assembly is sealed shut (hermetic) with respect to any external fluids and gases with would cause oxidation and deterioration of one or more of the plurality of rotor bearing magnet(s) 241, the plurality of rotor motor magnet(s) 244, and the rotor motor back iron 245.

In addition, the impeller shell 220 includes at least one impeller blade(s) 222, which are radially outward projections from a distal impeller shell interface 233 that are approximately helical and also angled with respect to rotational axis 210. In this example, the radially outward projections include a plurality of impeller blade(s) 222, such as three impeller blades. However, it will be understood that more or fewer impeller blades may alternatively be used and still fall within the scope of the present disclosure Although this example depicts at least one impeller blade(s) 222 having a substantially constant pitch, an optimized blade profile could alternatively include a variable pitch. Each impeller blade(s) 222 includes a blade tip surface 224, which has a diameter having tight dimensional control.

Referring now to FIG. 13, a mid-plane enlarged sectional view of the ventricular assist device 10 according to an exemplary embodiment is depicted. In particular, FIG. 13 depicts the interplay between the main flow components including the frame 60, the guard 74, the stator assembly 100, and the rotor assembly 200. As rotor assembly 200 spins at a speed typically in the range of 1,000-10,000 RPM, the impeller blade(s) 222 pull blood from the distal end 40 to the proximal end 45 and through impeller zone 302. Fluid, such as blood, enters the annular inlet 300 at the distal end 40 and travels through the collector zone 301. The blood also enters the frame 60 through the plurality of radial fenestrations 42 as the blood is pulled into an impeller zone 302. As the blood passes the plurality of impeller blade(s) 222, most of the blood exits frame 60 through the outlet 46. The blood further travels downstream as it is directed through at least one diffuser zone, and in one example, a plurality of diffuser zone(s) 72, disposed at the proximal end. Thus, as depicted in FIG. 13, a primary flow path 320 of the ventricular assist device 10 is defined by the annular inlet 300, the collector zone 301, the impeller zone 302, the plurality of radial fenestrations 42 in the frame 60, the at least one diffuser zone 72, and the annular outlet 46.

Some of the blood that is directed through the impeller zone 302 is further directed through an axial rotor gap 303 disposed between the frame 60 and the rotor assembly 200 and then through a radial rotor gap 304 disposed between the stator assembly 100 and the rotor assembly 200. The blood that gets ingested through this annular space is directed in a retrograde fashion from the proximal end 45 to the distal end 40 through the radial rotor gap 304 and then subsequently through a convergence zone 305 to a bearing bypass zone 306 and through the plurality of through-holes 204 of the rotor assembly. Thus, and as depicted in FIG. 13, a secondary flow path 340 of the ventricular assist device 10 is defined by the annular inlet 300, the collector zone 301, the impeller zone 302, the axial rotor gap 303, the radial rotor gap 304, the convergence zone 305, the bearing bypass zone 306, and the plurality of through-holes 204. So configured, the fluid, such as blood, is drawn through the annular inlet 300 disposed at the distal end 40 and also exits through the plurality of through-holes 204 of the rotor assembly 200, which are likewise disposed at the distal end 40. Said another way, in the secondary flow path 340, the blood is both drawn through the annular inlet in the distal end 40 and ultimately exits through the plurality of through-holes 204 disposed near the distal end 40. This is in contrast to the primary flow path 320 of the device 10 in which fluid, such as blood, is drawn through the annular inlet 300 disposed at the distal end 40 and exits through the annular outlet 440 disposed at the proximal end 45.

This retrograde blood flow through the secondary flow path 340 serves to wash out an annular gap disposed between the stator assembly 100 and the rotor enclosure 200 for preventing thrombus. In the addition, the secondary blood flow path 340 also serves to cool the stator assembly 100 from heat generated by the motor stator 101 as it is energized while the device 10 is operating. The blood accumulates within this secondary flow path 340 in the bearing bypass zone 306, which is proximal to thrust bearing interface 310, and exits through the plurality of through hole(s) 204, which are depicted in FIGS. 12A-12B. Blood flow near thrust bearing interface 310 that passes through the rotor assembly 200 that exits at the distal end 40 also serves to cool the surfaces near the thrust bearing interface 310 from heat generated by relative rotation of the rotor assembly 200 with respect to stationary stator assembly 100. The blood flow rate through the secondary flow path 340 as described is a small fraction of the overall blood flow rate through impeller zone 302 of the primary flow path 320

In operation, the motor stator assembly 101 is electrically controlled and commutated by the controller 12 (FIG. 1) connected through the lead 80 extending from the proximal end 45. The small gap between the motor stator assembly 101 and the rotor motor magnet(s) 244 of the rotor assembly 200 enables efficient motor operation including maintaining speed or modulating speed in a cyclical fashion of repeated acceleration and deceleration in a pulsatile mode.

A motor including the motor stator assembly 101 and the plurality of rotor motor magnet(s) 244 are located between the thrust bearing interface 310 toward the distal end 40 and the plurality of stator bearing magnet(s) 121 and the rotor bearing magnet(s) 241, which together comprise a radial magnetic bearing positioned near the proximal end 45 of the rotor assembly 200. Still referring to FIG. 13, arrows designating a magnetization of the stator bearing magnets 241 and the plurality of the rotor bearing magnet(s) 241, which alternate directionally, are depicted. In addition, the plurality of stator bearing magnet(s) 121 are stacked together to create an alternating magnetic field. The alternating magnetic field of the plurality of stator bearing magnets 121 interacts with an alternating magnetic field created by the plurality of rotor bearing magnet(s) 241 that are stacked in a similar arrangement of alternating polarity. As a result, these two alternating magnetic fields of high density and force support the proximal end 45 of the rotor assembly 200 in a substantially coaxial relationship with respect to the stator assembly 100. In addition, at the proximal end 45 of the rotor assembly 200, the plurality of stator bearing magnet(s) 121 that are in magnetic opposition to the plurality of rotor bearing magnet(s) 241 provide a radial bearing support. The radial stiffness of the magnetic bearing is not nearly to the same extent as a contact bearing, but provides sufficient support without needing to use a contactless bearing.

It can further be understood at least from FIG. 13 that the axial position of the plurality of rotor bearing magnet(s) 241 are slightly offset with respect to the plurality of stator bearing magnet(s) 121 in the direction of the proximal end 45. This axial offset of the magnetic radial bearing components produces an axial force that serves to bias the rotor assembly 200 toward the proximal end 45. In addition, this axial offset configuration is optimized to ensure that under various operating conditions, including trust forces produced by the pumping action of the rotor assembly 200, that contact between the rotor assembly 200 and the stator assembly 100 is maintained along the thrust bearing interface 310. The goal with an optimized design is to ensure a sufficient axial biasing force yet not an excessive contact force at the thrust bearing interface 310 that would cause excessive friction, heating, and wear along the thrust bearing interface 310. It is further understood that the thrust bearing interface 310 provides at the distal end 40 both axial and radial bearing support to the rotor assembly 200 limiting axial and radial movement of the rotor assembly 200 at the distal end 40 as the rotor assembly 200 rotates.

During initial starting or accelerating or slowing down, the rotor assembly 200 may wobble off an axis relative to the stator assembly 100 near the distal end 40. A benefit of this exemplary embodiment is that the possibility of intermittent contact of the internal surface of the rotor assembly 200 contacting the outer surface of the stator assembly 100 near the proximal end 45 would be of little consequence at least because both surfaces are preferably zirconia ceramic. As a result, minor intermittent contact between these two surfaces, e.g., the internal surface of the rotor assembly 200 and the outer surface of the stator assembly 100, would do little to damage the surfaces and/or cause any increased roughness as would otherwise be the case if the contacting surfaces (or other components) were made of a titanium alloy or other metal.

As further depicted in FIG. 13, the blade tip surfaces 224 are at the ends of the plurality of impeller blade(s) 222 of the rotor assembly 200 and there is a gap between the blade tip surfaces 224 and the shroud inner surface 64 of the frame 60. This gap is sufficiently large to avoid excessive blood shear as the rotor assembly 200 spins with the frame 60 remaining stationary. Blood shear associated by the impeller blade(s) 222 spinning near a stationary surface is indicative of hemolysis. Thus, the goal is to maximize the gap between blade tip surfaces 224 and shroud inner surface 64, but not to the extent that efficiency of the pump mechanism is substantially diminished. It can also be seen that the shroud 63 of the frame 60 and the guard 74 guard and prevent the rotor assembly 200 (rotating at high velocity) from contact with any adjacent structures including surrounding anatomy.

Still referring to FIG. 13, the preferred assembly sequence of the overall ventricular assist device 10 is understood as follows. First, the stator assembly 100 is inserted into the frame 60, and they are laser welded together along weld seam 250. Second, the rotor assembly 200 is inserted over the stator assembly 100 from the distal end 40. The rotor assembly 200 must be guided with sufficient force to overcome the magnetic interactions between the plurality of stator bearing magnet(s) 121 and the rotor bearing magnet(s) 241 to snap into the appropriate position. Third, the guard 74 is attached to the frame 60, and they are joined by laser welding along the seam 77. Fourth, the anchor 50 is inserted over the frame 60 from the proximal end 45, and the annular base 51 of the anchor 50 is snapped into instances of the proximal slot(s) 67 incorporated as part of the frame 60 (as described above). Because the plurality of proximal projection(s) 68 are interrupted by the plurality of diffuser zone(s) 72, the annular base 51 of the anchor 50 has the freedom to temporally assume a non-circular geometry as the annular base 51 is forced over the plurality of proximal projection(s) 68 to snap and be retained in the plurality of outlet slot(s) 67. Once the annular base 51 is appropriately positioned within the plurality of proximal slot(s) 67, the annular base 51 assumes a substantially circular geometry. Accordingly, the anchor 50 can be readily secured to the frame in a way that is secure and subject to minimal failure potential. This due at least to the fact that the interface is a snap fit rather than a bond or braze joint attempting to join dissimilar material, as nitinol (the preferred material for the anchor 50) cannot be laser welded to a titanium alloy (the preferred material for the frame 60).

Alternative embodiments to the invention may incorporate greater or fewer magnets for radial bearing support of the rotor assembly 200 near the proximal end 45. Additionally, the ventricular assist device 10 may also be able to function without any of the stator bearing magnet(s) 121 or the rotor bearing magnet(s) 241, as depicted in FIGS. 14 and 15 and further explained below. In this example, the rotor assembly 200 is then supported at the aortic arch 26 by fluid forces through the radial rotor gap 304, as further explained below. Thus, the radial bearing means could be hydrodynamic rather than magnetic. Moreover, the radial bearing support can also be provided by combination of the fluid and magnetic forces working substantially in tandem in a "hybrid" manner and still fall within the scope of the present disclosure In addition, and for proposes of providing an axial biasing force to the rotor assembly 200, alternative embodiments may include an axial offset of the rotor motor magnet(s) 244 relative to the motor stator assembly 101. In this configuration, the interaction of the motor stator assembly 101 with the rotor motor magnet(s) 244 results in an axial biasing force. Alternatively, dedicated magnets may be incorporated in various locations of the stator assembly 100 and the rotor assembly 200 for providing an axial biasing force.

Still referring to FIG. 13, the implementation of an alternative bearing design at the thrust bearing interface 310 between the stator assembly 100 and the rotor assembly 200 near the distal end 40 would not depart from the scope of the present invention. Rather than a semi-spherical ball and cup geometry of the thrust bearing, alternative thrust bearing designs that still serve to axially support the rotor assembly 200 as it spins may alternatively be used. As an alternative to the thrust bearing interface 310 that is associated with mechanical contact, the axial thrust bearing may also rely on fluid forces to ensure axial support while avoiding mechanical contact between the stator assembly 100 and the rotor assembly 200.

Referring now to FIGS. 14 and 15, another ventricular assist device 400 according to an alternative exemplary embodiment of the present disclosure is depicted. The ventricular assist device 400 includes a length of the blood pump, e.g., the rotor assembly 200, that is reduced and an orientation of the blood pump that is reversed compared to the ventricular assist device 10 described above. The ventricular assist device 400 configuration is a "transvalvular" embodiment in which the lead 80 passes through the aortic valve and is shown in context with a posterior sectioned illustration of a human heart. For reference, and as also referenced relative to the device 4000, the anatomical features of the heart 20 are again designated as the left ventricle 21, the right ventricle 22, the aortic valve 23, the coronary artery 24, the ascending aorta 25, the aortic arch 26, the pulmonary artery 27, the brachiocephalic artery 28, the aortic root 29, the lesser curve 30, and the greater curve 31. In addition, parts of the ventricular assist device 400 of FIGS. 14 and 15 that are the same as parts of the ventricular assist device 10 of FIGS. 1-13 include the same reference numbers and, therefore, are generally not described again in detail here relative to the alternative ventricular assist device 400.

Referring now to FIG. 14, the device 400 includes the distal end 40 and the proximal end 45 with the lead 80 extending from proximal end 45 through the aortic valve. Preferably, in this example, the lead 80 passes through left ventricle 21 and passes through the myocardial wall near the left ventricular apex 32 of the heart. Like the ventricular assist device 10, the primary structural components of device 400 include the frame 60 with the anchor 50 affixed thereto, as described above. The frame 60 is adapted for contacting and supporting the device in location within the artery. The proximal end 40 of frame 60 is near the aortic root 29 in relatively close proximity to the aortic valve 23. In the reverse orientation as compared to the device 10 of FIGS. 1-13, the device 400 of FIG. 14 augments blood flow by receiving blood near the proximal end 45 and ejecting blood near the distal end 40 in a primary flow path of the device 400. In addition to blood flowing through the device 400, blood may also flow in an annular space around an outside of the frame 60 to bypass the pump mechanism within the frame 60.

In further reference to FIG. 14, the anchor 50 of the device 400 is constrained in a collapsed configuration during the surgical procedure and then deployed into the optimal position. In this embodiment, the device 400 may be deployed via a delivery catheter (not shown) that is routed through the left ventricle 21 and the aortic valve 23. When the delivery catheter (not shown) is removed, the lead 80 remains routed through the myocardial wall at the incision site near the left ventricular apex 32. Alternatively, the device 400 may be delivered through an incision side along the greater curve 31, with only the lead 80 being directed through a second incision near the left ventricular apex 32. The anchor 50 is then allowed to expand to hold the device 400 to ascending aorta 25 in the approximate position indicated. Accordingly, the device 400 is positioned upstream from the aortic arch 26 at a relatively straight luminal position of the ascending aorta 25 before curvature associated with the lesser curve 30 and the greater curve 31. The lead 80 is flexible and follows a curved path through the aortic valve 23 and left ventricle 21. The lead 80 is of a sufficient length (full length not shown) to extend to a controller 12 (see, e.g. FIG. 1) that provides power to the device 400 and controls the operational speed of the rotor assembly 200. The controller 12 may be located inside or outside the patient's body.

As will be appreciated, the alternative device 400 of FIG. 14-15, as compared to the device 10 of FIGS. 1-13, is of a reduced axial length and can better be accommodated within the ascending aorta 25. In the alternative device 400, the axial length of the anchor 50 is approximately equivalent to the axial length of the frame 60, and a portion of the rotor assembly 200 extends from the distal end 40 in the downstream direction of the device 400, e.g., the blood pump. In one example, the approximate axial length of the anchor 50 and the frame 60 of the device 400 of FIGS. 14-15 are approximately 16 mm, as compared to the approximate axial length of the anchor 50 and the frame 60 of the device 10 of FIGS. 1-13 being approximately 28 mm in length. This corresponds to a reduction of about 43% in axial length of the larger diameter structural elements in this example. As will be appreciated, the approximate axial length of the anchor 50 and the frame 60 of the device 400 may alternatively be greater than 16 mm and still less than the 28 mm of the device 10 and still fall within the scope of the present disclosure, and, in particular, the inventive features of the device 400

Referring now to FIG. 15, a mid-plane enlarged sectional view of the device 400 according to the alternative embodiment of the present disclosure is depicted. In particular, the main flow components of the device 400, including the frame 60, the stator assembly 100, and the rotor assembly 200 are depicted. As opposed to the device 10 of FIGS. 1-13, in the device 400 blood is drawn into the impeller zone 302 through instances of the proximal slots 47 disposed at the proximal end 45 and ejected from the annular outlet 308 at the distal end 40. As blood is ingested through proximal slots 67, the blood flows through the impeller zone 302 and exits the annular outlet 308. Thus, a primary flow path 420 of the device 400 is defined by the at least one proximal slot 67 disposed at the proximal end 65 of the frame 60, the impeller zone 302, and the annular outlet 308 disposed at the distal end 40 of the frame 60.

Some blood near the distal end 40 is ingested into the rotor assembly 200 through holes 204 (not shown) and enters into the collector zone 309. The blood directed through the collector zone 309 is further directed through the annular rotor gap 304 between the stator housing 110 and the rotor housing 201. The blood then flows through the axial gap 303 at the proximal end 45 of the rotor assembly 200 and gets flushed out into a portion of the primary flow path 420. Thus, a secondary flow path 440 is defined by the plurality of through-holes 204 of the rotor assembly 200, the collector zone 309, the annular rotor gap 304, the axial gap 303, the impeller zone 302, and back out of annular outlet 308 at distal end 40 of the frame 60.

This secondary blood flow path 440 serves to wash out the annular gap between the stator assembly 100 and the stator assembly 200 for preventing thrombus and serves to cool the stator assembly 100 from heat generated by the motor stator 101 as it is energized while the device 400 is operating. Blood flow near the thrust bearing interface 310 that passes through the rotor assembly 200 and enters primary flow path 420 at axial gap 303 serves to also cool the surfaces near the thrust bearing interface 310 from heat generated by relative rotation of the rotor assembly 200 with respect to stationary stator assembly 100. The blood flow rate through the secondary flow path 440 as described is a small fraction of the overall blood flow rate through the impeller zone 302 of the primary flow path 420.

It will be further understood by reference to FIG. 15, in contrast to the device 10 of FIGS. 1-13, that there are no radial bearing magnets in the device 400. Instead, fluid forces are utilized to maintain radial support of the rotor assembly 200 as it spins in the device 400. The size of the annular gap 304 is optimized to provide a hydrodynamic bearing. Additional features may be added within the journal to contribute to fluid stiffness such as interrupting the cylindricity of the journal at various places to minimize fluid instability. By eliminating the plurality of radial bearing magnets in both the stator assembly 100 and the rotor assembly 200, the axial length of the device 400 is substantially reduced. The motor stator 101 of the stator assembly 100 interacts with the motor magnets 244 of the rotor assembly 200 to effect rotation of the rotor assembly 200 while the secondary flow path 440 geometry within the axial flow gap 304 is responsible for radial support of the proximal end 45 of the rotor assembly 200.

In addition to reduced length, the alternative device 400 of FIGS. 14-15 provides several additional advantages including reduced overall weight, reduced rotor inertia, a shorter secondary flow path 440 and lower manufacturing cost. The reduced rotor inertia and mass is advantageous in the sense that less power is required to accelerate and decelerate the rotor assembly 200 when operating in a pulsatile mode of operation in which the speed is modulated over the cardiac cycle. The reduced power results in less heat along the blood contacting surfaces of the stator housing 100 and extended battery life for powering the device 400.

In the device 400 of FIGS. 14-15, the axial thrust forces generated by rotation of the rotor assembly 200 will act in the proximal direction causing an increased contact pressure at the thrust bearing interface 310 with increasing speed. Thus, minimal axial preload is needed to ensure contact of the rotor assembly 200 with the stator assembly 100 over the full range of operating conditions. A small axial preload can be established by an axial offset of motor magnets 244 with respect to motor stator 101. The magnetic interplay between these will cause a magnetic force in the axial direction to maintain contact of the rotor assembly 200 with the stator assembly 100 when the device 400 is stopped or operating at a low speed.

Referring again to FIG. 15, the preferred assembly sequence of the device 400 includes the following steps. First, the stator assembly 100 is inserted into the frame 60, and they are laser welded together along weld seam 250. Second, the rotor assembly 200 is inserted over the stator assembly 100 from the distal end 40. Third, the anchor 50 is inserted over the frame 60 from the proximal end 45 and the annular base 51 of the anchor 50 is engaged with frame 60. Because the plurality of proximal projection(s) 68 are interrupted by the plurality of diffuser zone(s) 72, the annular base 51 of the anchor 50 has the freedom to temporally assume a non-circular geometry as the annular base 51 is forced over the plurality of proximal projection(s) 68 to snap and be retained in the plurality of proximal slot(s) 67. Once the annular base 51 is appropriately positioned within the plurality of proximal slot(s) 67, the annular base 51 assumes a substantially circular geometry.

As compared to the device 10 of FIGS. 1-13, the alternative device 400 of FIGS. 13-15 is characterized with fewer components and fewer assembly steps. The stator housing 100 and the rotor housing 200 are preferably made of zirconia ceramic for the same reasons stated previously relative to the device 10, for example. However, zirconia is a very hard material and machining such precision components out of ceramic comes at significant cost as compared to a metal alloy. Substantially reducing the axial length of these components also serves to reduce the cost of what is likely the most expensive components of the device 400.

Having described the structure and operation of the above-described ventricular assist devices 10, 400, exemplary methods of implantation are further discussed below. Generally, and referring back to FIG. 1, the device 10 is depicted disposed through an incision in the greater curve 31 and positioned within the ascending aorta 25. The lead 80 exits normal to the aortic wall along the greater curve 31. In contrast, and referring back to FIG. 14, the device 400 is depicted disposed through an incision in the left ventricle 21 and, thus, routed through the left ventricle 21 and the aortic valve 23. The lead 80 extends through the myocardial wall at the incision site near the left ventricular apex 32.

More specifically, and referring back to FIG. 1, for example, the method of implanting the device 10 in a human heart comprises the steps of selecting the frame 60 sized for placement within a blood vessel at a selected location within the blood vessel. As explained above, the frame 60 incudes the inner surface defining the flow path, the stator assembly 100 disposed within the frame 60, and the rotor assembly 200 disposed between the frame 60 and the stator assembly 100. The method further comprises attaching the base 51 of the anchor 50 to the proximal end 45 of the frame 60 and placing the anchor 50 at the selected location in a collapsed configuration. This includes placing the anchor 50 through an incision in the greater curve 31 of the human heart and positioning the anchor 50 within the ascending aorta 25. The method further includes expanding the anchor 50 at the selected location to secure the frame 60 to the selected location and operatively coupling the power source to the stator assembly 100.

In some examples, placing the anchor 50 of the device 10 at the selected location in a collapsed configuration comprises positioning the anchor 50 upstream from the aortic arch 26 at a luminal position of the ascending aorta 25 before a curvature associated with the lesser curve 30 and the greater curve 31 of the human heart. In another example, placing the anchor 50 at the selected location in a collapsed configuration may comprise bending the lead 80 extending from the proximal end 45 of the frame 60 within the ascending aorta 25 to exit normal to an aortic wall along the greater curve 31 of the human heart.

Referring back to FIG. 14, the method of implanting the ventricular assist device 400 comprises the steps of selecting the frame 60 sized for placement within a blood vessel at a selected location within the blood vessel. In this example, the frame 60 again includes an inner surface defining a flow path, and the stator assembly 100 is disposed within the frame 60. The rotor assembly 200 is again disposed between the frame and the stator assembly. The method also includes attaching the base 51 of the anchor 50 to the proximal end

45 of the frame 60 and placing the anchor 50 at the selected location in a collapsed configuration. This includes further routing the anchor 50 attached to the frame 60 through the left ventricular apex 32 and into an aortic valve 23 of a human heart. The method also includes expanding the anchor 50 at the selected location to secure the frame 60 to the selected location, operatively coupling a power source to the stator assembly 100, and controlling the power source to cause the rotor assembly 200 to rotate.

In some examples, placing the anchor 50 at the selected location in a collapsed configuration further comprises extending the lead 80 from the proximal end 45 of the frame 60 and through a myocardial wall near the left ventricular apex 32. In another example, placing the anchor 50 at the selected location in a collapsed configuration may comprise placing the anchor 50 upstream from the aortic arch 26 at a luminal position of the ascending aorta 25 before a curvature associated with the lesser curve 30 and the greater curve 31 of the human heart.

While the selected location described above is the aorta, which allows the device 10, 400 to function as a left ventricular assist device, the selected location may alternatively be the pulmonary artery, which allows the device 10, 400 to function as a right ventricular assist device, for example. As a result, it will be understood that the device 10, 400 may function as an aortic or pulmonary valve. For example, the device 10, 400 could be considered in place of a mechanical valve in circumstances where there are problems with the native aortic or pulmonary valves when associated with severe cardiac failure of the left or right ventricles, respectively. Thus, the device 10, 400 is sized for placement/to fit within the selected cardiac artery, which may be, for example, the aorta or the pulmonary artery. By way of example, the diameter of the aorta and the pulmonary artery may be approximately 2.0 to 3.0 cm, with the diameter of each varying from individual to individual and even varying for the individual over the life of the individual, for example. In addition, the device 10, 400 may also prove suitable for use elsewhere in the vasculature.

Further, based on clinical judgment, if there are anatomical or medical constraints, the device 10, 400 may be placed in the descending aorta. More generally, because of the ability of the device 10, 400 to be located in any major vessel, the device 10, 400 could also be used as a peripheral circulatory assist device for severe peripheral vascular disease. In that iteration, the device 10, 400 could be placed in the descending aorta or in the femoral or iliac vessels and thus augment blood flow to the lower limbs. Similarly, the device 10, 400 could be placed in other locations within the aorta to augment blood flow in the relevant vascular beds. For instance, in individuals with severe peripheral vascular disease, placement of the device in the infra-renal position would augment natural blood flow and increase perfusion of the lower limbs. In critical lower limb ischemia, improvement of a proximal blood flow may allow the ability to treat the lower limb ischemia. In yet another example, there may be a generational miniaturization of the device 10, 400, which would also allow for the possibility of using the device 10, 400 for augmentation of the peripheral circulation in peripheral vascular disease.

Still further, and in another example, the device 10, 400 may alternatively be secured to the blood vessel using other suitable means, such as a graft. Specifically, the device 10, 400 may alternatively be placed within a vascular graft, such as a Dacron or PTFE, or any other suitable vascular graft, which can then be anastomosed side to side in the ascending aorta, the descending aorta, or within the aorta itself. In addition, with the use of the vascular graft, the device 10, 400 may then be placed as a unit at the desired location using any suitable delivery technique, such as a trans-apical approach. In turn, the vascular graft may be suitably secured to the surrounding blood vessel using conventional techniques. For example, the graft may be sutured to the surrounding vessel, the graft may be secured using conventional stent securing techniques, or magnetic securement such as magnetic rings. Still other means may prove suitable.

In addition, the control of power and settings of the device 10, 400 may include using a near field communication system to control the power requirements and output, the timing, or other settings. Such as approach may employ wireless cell phone technology, or other suitable technology, as a means of communication with a control unit. Thus, the control system would not need any sort of cable or wired connection, and programming may be accomplished with hand-held devices, such as through a cell phone or other module. The device and its control system would be completely implantable.

In accordance with all the forgoing description, it will be appreciated that the devices and methods of the present disclosure achieve several advantages including minimum size and volume as well as enclosures pertaining to the stator assembly and the rotor assembly that provide a sleeve or barrier to hermetically seal and insulate internal components from any harmful exposure to moisture and/or any gas that would otherwise cause degradation and corrosion of materials and components housed within. In addition, the devices and methods of the present disclosure include device architecture that is also of minimum size and length, which facilitates the durability and long-term reliability as is necessary for an active implant with passive magnetic, active magnetic and electrical components. It will also be appreciated that the devices and methods of present disclosure attain an optimal form factor and implementation of an anchor that is well suited for placement and fixation within the ascending aorta or other segment of blood vessel that is relatively short in length.

It will be also appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A ventricular assist device for a human heart, the device comprising:
a frame having a proximal end;
an anchor coupled to the proximal end of the frame and moveable between a collapsed configuration and an expanded configuration, the expanded configuration a configuration in which a portion of the anchor is offset from the frame and engages a portion of a blood vessel;
a stator assembly disposed within the frame, the stator assembly comprising a stator housing having a sleeve, a thrust bearing surface integral with the sleeve, and an internal area;
a rotor assembly disposed between the stator assembly and the frame; and
a power source operatively coupled to the stator assembly, the stator assembly and the rotor assembly arranged to interact in response to the application of power from the power source to the stator assembly, where the stator housing defines a hermetically sealed assembly, sealing off the internal area of the stator housing, and the thrust bearing surface is a convex thrust bearing surface.

2. The device of claim 1, the stator housing comprising ceramic material.

3. The device of claim 1, the stator housing further comprising a thrust bearing including the thrust bearing surface, the thrust bearing integral with the sleeve of the stator housing and having a semi-spherical shape.

4. The device of claim 1, the stator housing further comprising an expansion surface outwardly extending from the thrust bearing surface and toward the sleeve, the expansion surface integral with the thrust bearing surface and the sleeve, the sleeve having an outer surface.

5. The device of claim 1, the stator housing further comprising a proximal end, a distal end, a flange portion disposed at the proximal end, the thrust bearing surface disposed at the distal end and having a convex shape, and a housing bore open at the proximal end and for receiving a motor stator assembly.

6. The device of claim 1, the stator housing further comprising a ring coupled to a joint disposed at proximal end of the stator housing, the ring comprising a titanium material, and the joint between the flange and the ring comprising a gold material, and the device further comprising a feedthrough assembly welded to the ring and forming a weld seam.

7. The device of claim 1, further comprising a motor stator assembly, the motor stator assembly disposed within the internal area of the stator housing and comprising one or more of: a support tube having a bore; a plurality of holes at each end of the support tube; a plurality of laminations assembled over the support tube in a central position; an end spacer disposed at each end of the support tube; and a plurality of windings, where the end spacer enables the plurality of windings to be coupled to the plurality of laminations without abrasion to the plurality of windings.

8. The device of claim 7, wherein each winding of the plurality of windings includes loops of magnet wire, the plurality of holes at each end of the support tube allowing ends of magnet wires to be disposed there through and into the bore without obstructing the ends of the support tube.

9. The device of claim 1, the device adapted to be coupled to a controller having a power source, and a sensor operatively coupled to the controller, wherein the controller is programmed to operate the power source to provide a pulsatile flow, to use the sensor to determine native cardiac rhythms, and to control the rotational speed of the rotor in response to the native cardiac rhythms.

10. A ventricular assist device for a human heart, comprising:
a frame having a proximal end, a distal end, a plurality of fenestrations, and an external surface;
an anchor coupled to the proximal end of the frame and adapted to engage a portion of a blood vessel;
a stator assembly disposed within the frame;
a rotor assembly disposed between the stator assembly and the frame, the rotor assembly including an impeller shell;
a power source operatively coupled to the stator assembly, the stator assembly and the rotor assembly arranged to interact in response to the application of power from the power source to the stator assembly;
a primary flow path defined by an annular inlet disposed at the distal end of the frame, the plurality of fenestrations in the frame, an impeller zone disposed between an external surface of the frame and the impeller shell of the rotor assembly, and an annular outlet disposed at the proximal end of the frame, such that fluid in the primary flow path is drawn through the annular inlet and the plurality of fenestrations into the impeller zone, and exits out of the annular outlet disposed at the proximal end;

a secondary flow path defined by the annular inlet, the impeller zone, an axial rotor gap disposed between the frame and the rotor assembly, a radial rotor gap disposed between the stator assembly and the rotor assembly, and a plurality of through-holes of the rotor housing, such that fluid in the secondary flow path is drawn through the impeller zone and passes through the axial rotor gap, the radial rotor gap, and the plurality of through-holes of the rotor assembly, exiting at the distal end of the frame; and a thrust bearing disposed at the distal end of the frame, the thrust bearing comprising a convex thrust bearing surface of the stator assembly that fits into a concave thrust bearing surface of the rotor assembly.

11. The device of claim 10, the secondary flow path further defined by one or more of a convergence zone at the distal end of the frame and a bearing bypass zone, such that fluid in the secondary flow path also passes through the convergence zone and the bearing bypass zone.

12. The device of claim 10, where the power source is a motor stator assembly disposed within the stator assembly, the motor stator assembly coupled to a controller by a lead extending from the proximal end of the frame, the controller for electrically controlling the motor stator assembly.

13. The device of claim 12, the stator assembly includes a plurality of stator bearing magnets disposed near the proximal end, and the rotor assembly further comprises a plurality of rotor bearing magnets disposed near the proximal end, such that the plurality of stator bearing magnets and the plurality of rotor bearing magnets together comprise a radial magnetic bearing positioned near the proximal end of the rotor assembly.

14. The device of claim 13, where the plurality of stator bearing magnets are axially magnetized and stacked in opposing polarity, and the plurality of rotor bearing magnets are axially magnetized and stacked in opposing polarity, the stator bearing magnet and the rotor bearing magnet interacting and creating a radial magnetic field to support the proximal end of the rotor assembly in a substantially coaxial position relative to the stator assembly.

15. The device of claim 10, the stator assembly including a plurality of stator bearing magnets and the rotor assembly including a plurality of rotor bearing magnets, such that at least one stator bearing magnet and at least one rotor bearing magnet are in magnetic opposition to each other, providing a radial bearing support.

16. The device of claim 10, the stator assembly including a plurality of stator bearing magnets and the rotor bearing assembly including a plurality of rotor bearing magnets, wherein an axial position of the plurality of rotor bearing magnets is offset relative to an axial position of the plurality of stator bearing magnets toward a proximal end, producing an axial force that biases the rotor assembly toward the proximal end and ensures contact between the stator assembly and the rotor assembly is maintained along a thrust bearing surface.

17. The device of claim 10, the convex thrust bearing surface includes a semi-spherical ball shape and the concave thrust bearing surface includes a cup-shape, the thrust bearing surface interface disposed between the convex thrust bearing surface and the concave thrust bearing surface.

18. The device of claim 17, wherein substrate material defining each of the concave thrust bearing surface of the rotor assembly and the convex thrust bearing surface of the stator assembly is zirconia ceramic.

19. The device of claim 10, wherein the distal end of the frame is adapted to be disposed near an aortic root proximate to an aortic valve and downstream from a coronary artery.

20. The device of claim 10, the device adapted to be coupled to a controller having a power source, and a sensor operatively coupled to the controller, wherein the controller is programmed to operate the power source to provide a pulsatile flow, to use the sensor to determine native cardiac rhythms, and to control the rotational speed of the rotor in response to the native cardiac rhythms.

* * * * *